United States Patent
Bowman et al.

(10) Patent No.: US 9,701,792 B2
(45) Date of Patent: Jul. 11, 2017

(54) COMPOSITE COMPOSITIONS AND METHODS OF PREPARING AND USING SAME

(71) Applicant: THE REGENTS OF THE UNIVERSITY OF COLORADO, A BODY CORPORATE, Denver, CO (US)

(72) Inventors: Christopher N. Bowman, Boulder, CO (US); Christopher J. Kloxin, Newark, DE (US); Jeffrey Stansbury, Centennial, CO (US); Tao Gong, Superior, CO (US); Matthew McBride, Boulder, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 14/663,015

(22) Filed: Mar. 19, 2015

(65) Prior Publication Data

US 2015/0267002 A1 Sep. 24, 2015

Related U.S. Application Data

(60) Provisional application No. 61/955,552, filed on Mar. 19, 2014.

(51) Int. Cl.
| | | |
|---|---|---|
| C08F 2/46 | (2006.01) | |
| C08F 2/50 | (2006.01) | |
| C08G 61/04 | (2006.01) | |
| C08G 73/08 | (2006.01) | |
| A61K 6/087 | (2006.01) | |
| A61K 6/083 | (2006.01) | |
| C08L 79/06 | (2006.01) | |

(52) U.S. Cl.
CPC ............ *C08G 73/08* (2013.01); *A61K 6/083* (2013.01); *A61K 6/087* (2013.01); *C08L 79/06* (2013.01)

(58) Field of Classification Search
USPC ............... 522/64, 6, 71, 189, 184, 1; 520/1
See application file for complete search history.

(56) References Cited

U.S. PATENT DOCUMENTS

| | | | |
|---|---|---|---|
| 6,395,124 B1 * | 5/2002 | Oxman | B32B 7/12 |
| | | | 156/275.5 |
| 6,727,034 B1 | 4/2004 | Ogiso et al. | |
| 2008/0045686 A1 | 2/2008 | Meagher et al. | |
| 2013/0323642 A1 * | 12/2013 | Bowman | C07D 249/04 |
| | | | 430/270.1 |

FOREIGN PATENT DOCUMENTS

WO    2012-074931    * 7/2012

OTHER PUBLICATIONS

Schunack et al, Low Temperature Cu(I) catalyzed "Click" reactions for self-healing polymers, Oct. 10, 2011, Macromol. Chem. Phys., 213, 205-214.*
Himo, et al., "Copper(I)-catalyzed synthesis of azoles. DFT study predicts unprecedented reactivity and intermediates", J Am Chem Soc.127(1), Jan. 12, 2005, 210-216.
Kunkely, et al., "Photoredox reactivity of copper(II)-3,5-diisopropylsalicylate induced by ligand-to-metal charge transfer excitation of the copper-phenolate chromophore", Inorganica Chimica Acta. 357(3), Feb. 20, 2004, 888-890.
Perera, "Development of clickable approaches to build functional polymeric nanoparticles", Thesis submitted to The University of Nottingham, The University of Nottingham School of Pharmacy, Nottingham, UK, Sep. 2009.
Ritter, "Cu(I)-catalyzed "click-chemistry" Design of a Chemical Photomultiplier Target-guided Synthesis of Bidentate Metal-complex Receptors", Thesis submitted to the University of Regensburg, Universität Regensburg, Germany, 2007.
Tasdelen, et al., "Light-induced copper(I)-catalyzed click chemistry", Tetrahedron Letters 51(52), Dec. 29, 2010, 6945-6947.

* cited by examiner

*Primary Examiner* — Jessica E Whiteley
(74) *Attorney, Agent, or Firm* — Saul Ewing LLP; Kathryn Doyle; Domingos J. Silva

(57) ABSTRACT

The present invention includes compositions comprising an alkyne-based substrate, an azide-based substrate, optionally a Cu(II) salt and optionally a photoinducible reducing agent. The present invention further includes a method of preparing composite materials that are suitable for use as dental implants using the compositions of the invention.

20 Claims, 8 Drawing Sheets

1,4-isomer     1,5-isomer

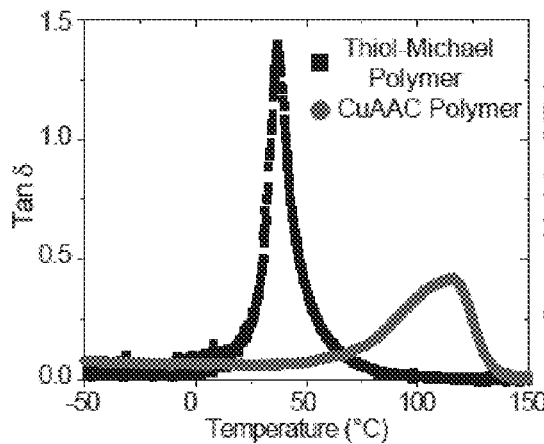
Fig. 4A
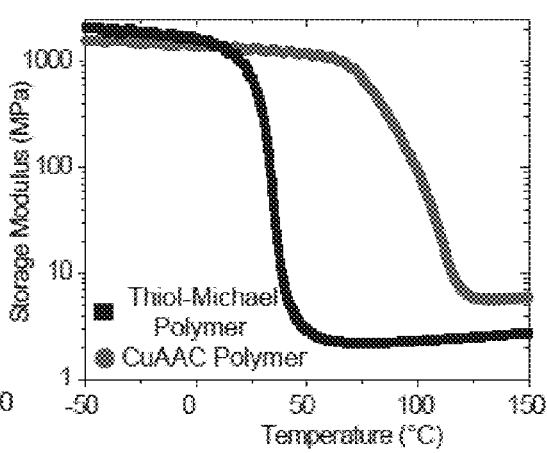
Fig. 4B
Fig. 5
Monomer Structure and Design:
C-(B-A)$_n$, n = 1- 4
| A) Functional Groups | B) Molecular Linkers | C) Monomer Core Structures |
|---|---|---|
| Alkyne | Alkyl | Alkyl |
| Azide | Heteroatom Alkyl  X = O, NH, etc | Cyclohexyl  n=1-4    Aromatic  n=1-4 |
| | Aromatic  Y = H, F, OCH$_3$, N(CH$_3$)$_2$, etc | Bisphenol A |
| | Thiocarbamate | |

1. Thiol-ene monomers

2. Photo-CuACC (aliphatic azide monomers)

3. Photo-CuACC (aromatic azide monomers)

COMPOSITE COMPOSITIONS AND METHODS OF PREPARING AND USING SAME

CROSS-REFERENCE TO RELATED APPLICATIONS

This application is entitled to priority under 35 U.S.C. §119(e) to U.S. Provisional Patent Application No. 61/955,552 filed Mar. 19, 2014, which application is hereby incorporated herein by reference in its entirety.

STATEMENT REGARDING FEDERALLY SPONSORED RESEARCH OR DEVELOPMENT

This invention was made with government support under grant number DE023774 awarded by the National Institutes of Health. The government has certain rights in the invention.

BACKGROUND OF THE INVENTION

More than 100 million dental restorations are performed each year, and at least 60% of those use polymerizable composites. Despite their ubiquitous presence in dentistry, polymerizable composites suffer from significant structural problems. Based on resin chemistry developed nearly 50 years ago, radically polymerizable dimethacrylate monomers have remained the monomers of choice in these composites.

The bisphenol A dimethacrylate (BisGMA)-based methacrylate resin is cured by light exposure, which causes radical formation. These radicals then mediate a chain-growth polymerization and conversion of methacrylates into crosslinked polymers, with the associated shrinkage and stress arising from conversion of monomer to polymer. Though most considerations of new dental restorative materials have focused on methacrylate modifications, this curing approach is flawed in ways not readily addressed without changing the composite nature. In particular, chain growth leads to a significant amount of residual, unreacted double bonds (and hence monomers) at the end of the polymerization. These monomers can be extracted and lead to non-desirable biological interactions. Further, methacrylates comprise esters that are unstable towards enzymes and high or low pH. Thus, most methacrylate-based systems may be limited in their ability for significant performance improvements.

Thus, problems inherent to the BisGMA system include, among others, the presence of extractable, unreacted monomer following cure, monomer and composite degradation, polymerization shrinkage and induced stresses, a lack of mechanical toughness and wear, and moisture uptake. The common result of these problems is premature failure of composites, resulting from secondary caries or mechanical failure of the bulk or the interface. With average lifetimes of only about 8 years for current restorative materials, there is great need to develop novel and improved composite materials for dental restorations.

The "click" reaction paradigm is centered on the development and implementation of robust reactions that proceed with reliable control over the products formed. A "click" reaction should have the following characteristics: the reaction involves minimal set-up effort and the starting materials are readily available; the reaction is high yielding, proceeding with high stereospecificity and high atom economy; the reaction is run solvent-free or in a benign solvent (preferably water); the product can be easily isolated by crystallization or distillation, preparative chromatography not being required; the by-products are easily removed and non-toxic; the reaction is physiologically compatible; and there is a large thermodynamic driving force (>84 kJ/mol) to favor the formation of a single reaction product.

One reaction that meets most of these criteria is the azide-alkyne Huisgen cycloaddition, which is a 1,3-dipolar cycloaddition between an azide and a terminal or internal alkyne to give a 1,2,3-triazole (Huisgen, 1961, Proc. Chem. Soc. London:357; Kolb et al., 2001, Angew. Chem.-Int. Edit. 40(11):2004-21).

A notable variant of the Huisgen 1,3-dipolar cycloaddition is the copper(I) catalyzed (or Cu(I)-catalyzed) variant, in which organic azides and terminal alkynes are united to afford 1,4-regioisomers of 1,2,3-triazoles as sole products (Tornoe et al., 2002, J. Org. Chem. 67:3057-64). While the Cu(I)-catalyzed variant gives rise to a triazole from a terminal alkyne and an azide, formally it is not a 1,3-dipolar cycloaddition and thus should not be termed a Huisgen cycloaddition. This reaction is known as the Cu(I)-catalyzed Azide-Alkyne Cycloaddition (CuAAC).

CuAAC is ubiquitous and highly efficient in an ever increasing number of synthetic methodologies and applications, including bioconjugation (Wang et al., 2003, J. Am. Chem. Soc. 125(11):3192; El-Sagheer & Brown, 2010, Chem. Soc. Rev. 39(4):1388); labeling (Macpherson et al., 2007, Nature 445(7127):541; Cohen et al., 2007, Nat. Chem. Biol. 3(3):156); surface functionalization (Spruell et al., 2008, Angew. Chem.-Int. Edit. 47(51):9927); dendrimer synthesis (Peng et al., 2004, Angew. Chem.-Int. Edit. 43(30):3928); polymer synthesis (DeForest et al., 2009, Nat. Mat. 8(8):659); and polymer modification (Matyjaszewski & Tsarevsky, 2009, Nat. Chem. 1(4):276). The diverse implementation of the CuAAC reaction is due to its simplicity, capability of high yield, fast reaction kinetics, orthogonal reactivity, and tolerance to a wide variety of solvent conditions. The CuAAC reaction may be run in a variety of solvents, such as aqueous solvents and (partially or fully) miscible organic solvents. The CuAAC reaction may be performed using commercial sources of Cu(I) such as cuprous bromide or iodide, or in situ sources of Cu(I), such as a mixture of Cu(II) (e.g. copper(II) sulfate) and a reducing agent (e.g. sodium ascorbate).

There is a need in the art to develop novel monomer systems that afford useful composite compositions once polymerized. Such polymerized composite compositions should have superior chemical and physical properties, allowing for their use in challenging applications, such as dental restorations. The present invention fulfills these needs.

BRIEF SUMMARY OF THE INVENTION

The invention includes a composition comprising an alkyne-based substrate, an azide-based substrate, optionally at least one Cu(II) salt and optionally at least one photoinducible reducing agent. The invention further includes a method of preparing a dental composite composition.

In certain embodiments, the alkyne-based substrate comprises at least one reactive alkynyl group. In other embodiments, the azide-based substrate comprises at least one reactive azide group. In yet other embodiments, the composition, when polymerized, is suitable for use as a dental composite.

In certain embodiments, the composition comprises at least one compound selected from the group consisting of

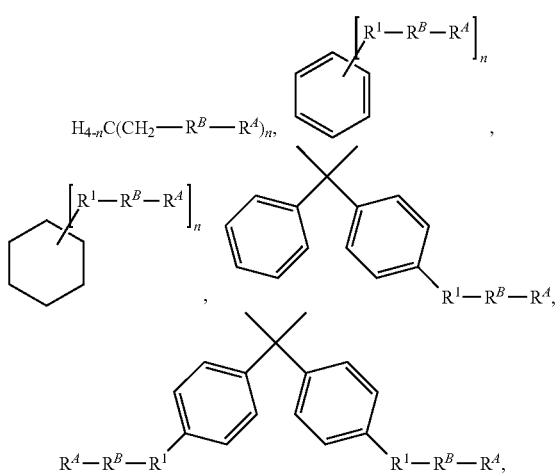

a salt or solvate thereof, and any combinations thereof, wherein: n=1-4; each occurrence of $R^1$ is independently a bond, —$CH_2$—, —O—, or —$NR^2$—; each occurrence of $R^2$ is independently H or $C_1$-$C_6$ alkyl; each occurrence of $R^B$ is independently $C_1$-$C_6$ alkanediyl, $C_1$-$C_6$ heteroalkanediyl; arenediyl, heteroarenediyl, —$(CH_2)_{0-4}$—NHC(=O)S—$(CH_2)_{0-4}$, or —$(CH_2)_{0-4}$—SC(=O)NH—$(CH_2)_{0-4}$—; wherein the alkanediyl, heteroalkanediyl, arenediyl and heteroarenediyl groups are optionally and independently substituted with one or more groups selected from the group consisting of OH, F, Cl, Br, I, alkyl, perfluoroalkyl, alkoxy, perfluoroalkoxy, $NH_2$, acylamino, amido, carboxyl, alkoxycarbonyl, acyloxy, formyl, acyl, thioester, carbamate, urea, sulfonate, sulfamoyl, sulfone, sulfonamide, CN, $NO_2$, and alkylthio; and, each occurrence of $R^A$ is independently $N_3$ or —C≡C—H.

In certain embodiments, the molar ratio of the at least one reactive alkyne group and the at least one reactive azide group in the composition is such that polymerization of the composition results in greater than about 80% conversion of at least one selected from the group consisting of the alkyne-based substrate and the azide-based substrate.

In certain embodiments, the molar ratio of the at least one reactive alkyne group and the at least one reactive azide group in the composition ranges from about 0.5 to about 2.

In certain embodiments, the alkyne-based substrate and the azide-based substrate are at least partially polymerized. In other embodiments, polymerization of the substrates is achieved by irradiating at least a portion of the composition with ultraviolet, visible or infrared electromagnetic radiation.

In certain embodiments, the composition comprises at least one Cu(II) salt. In other embodiments, the Cu(II) salt comprises at least one selected from the group consisting of copper(II) sulfate, copper(II) chloride, copper(II) bromide, copper(II) iodide, copper(II) perchlorate, copper(II) nitrate, copper(II) hydroxide, copper(II) oxide, and hydrates and mixtures thereof.

In certain embodiments, the composition comprises at least one photoinducible reducing agent. In other embodiments, the at least one reducing agent comprises at least one selected from the group consisting of: 1-hydroxy-cyclohexyl-phenyl-ketone (Irgacure 184); a 1:1 mixture of 1-hydroxy-cyclohexyl-phenyl-ketone and benzophenone (Irgacure 500); 2-hydroxy-2-methyl-1-phenyl-1-propanone (Darocur™ 1173); 2-hydroxy-1-[4-(2-hydroxyethoxy)phenyl]-2-methyl-1-propanone (Irgacure 2959); methyl benzoylformate (Darocur™ MBF); oxy-phenyl-acetic acid 2-[2-oxo-2-phenyl-acetoxy-ethoxy]-ethyl ester; oxy-phenyl-acetic 2-[2-hydroxy-ethoxy]-ethyl ester; a mixture of oxy-phenyl-acetic acid 2-[2-oxo-2-phenyl-acetoxy-ethoxy]-ethyl ester and oxy-phenyl-acetic 2-[2-hydroxy-ethoxy]-ethyl ester (Irgacure 754); alpha,alpha-dimethoxy-alpha-phenylacetophenone (Irgacure 651); 2-benzyl-2-(dimethylamino)-1-[4-(4-morpholinyl)-phenyl]-1-butanone (Irgacure 369); 2-methyl-1-[4-(methylthio)phenyl]-2-(4-morpholinyl)-1-propanone (Irgacure 907); a 3:7 mixture of 2-benzyl-2-(dimethylamino)-1-[4-(4-morpholinyl)phenyl]-1-butanone and alpha,alpha-dimethoxy-alpha-phenylacetophenone per weight (Irgacure 1300); diphenyl-(2,4,6-trimethylbenzoyl) phosphine oxide (Darocur™ TPO); a 1:1 mixture of diphenyl-(2,4,6-trimethylbenzoyl)-phosphine oxide and 2-hydroxy-2-methyl-1-phenyl-1-propanone (Darocur™ 4265); phenyl bis(2,4,6-trimethyl benzoyl) phosphine oxide (Irgacure 819, or Irgacure 819DW); a 2:8 mixture of phosphine oxide, phenyl bis(2,4,6-trimethyl benzoyl) and 2-hydroxy-2-methyl-1-phenyl-1-propanone (Irgacure 2022); phenyl-bis(2,4,6-trimethylbenzoyl)-phosphine oxide (Irgacure 2100); bis-(eta 5-2,4-cyclopentadien-1-yl)-bis-[2,6-difluoro-3-(1H-pyrrol-1-yl)phenyl]-titanium (Irgacure 784); (4-methylphenyl) [4-(2-methylpropyl)phenyl]-iodonium hexafluorophosphate (Irgacure 250); 2-(4-methylbenzyl)-2-(dimethylamino)-1-(4-morpholinophenyl)-butan-1-one (Irgacure 379); 4-(2-hydroxyethoxy)phenyl-(2-hydroxy-2-propyl)ketone (Irgacure 2959); bis-(2,6-dimethoxybenzoyl)-2,4,4-trimethylpentylphosphine oxide; a mixture of bis-(2,6-dimethoxybenzoyl)-2,4,4-trimethylpentylphosphine oxide and 2-hydroxy-2-methyl-1-phenyl-propanone (Irgacure 1700); acyl germane photonitiators; titanium dioxide; camphorquinone/amine systems; primary amines; and mixtures thereof.

In certain embodiments, the composition further comprises a Cu(I)-stabilizing ligand. In other embodiments, the Cu(I)-stabilizing ligand comprises at least one selected from the group consisting of TBTA (tris[(1-benzyl-1H-1,2,3-triazol-4-yl)methyl]amine); BTTES (2-4-(bis1-tert-butyl-1H-1,2,3-triazol-4yl) methylamino(methyl-1H-1,2,3-triazol-1-yl)ethanesulfonic acid); $N^1$-(2-(dimethylamino)ethyl)-$N^1$, $N^2$, $N^2$-trimethylethane-1,2-diamine; $N^1$,$N^2$-(ethane-1,2-diyl)bis($N^1$,$N^2$,$N^2$-trimethylethane-1,2-diamine); 2,2'-bipyridine, and any combinations thereof.

In certain embodiments, the composition further comprises at least one selected from the group consisting of a filler, bonding agent, coupling agent, and any combinations thereof. In other embodiments, the filler is functionalized with at least selected from the group consisting of an alkyne group and an azide group.

In certain embodiments, the composition further comprises a dimethacrylate monomer. In other embodiments, the dimethacrylate monomer comprises bisphenol A dimethacrylate (BisGMA) or triethyleneglycol dimethacrylate (TEGMA).

In certain embodiments, the composition further comprises a compatibilizer comprising an alkynyl group and an alkenyl group. In other embodiments, the compatibilizer is selected from the group consisting of prop-2-yn-1-yl methacrylate, prop-2-yn-1-yl acrylate, N-(prop-2-yn-1-yl)methacrylamide, N-(prop-2-yn-1-yl) acrylamide, N-methyl-N-(prop-2-yn-1-yl)methacrylamide, N-methyl-N-(prop-2-yn-1-yl) acrylamide, and any combinations thereof.

In certain embodiments, the method comprises photopolymerizing at least a portion of any at least partially unpolymerized composition of the invention, thereby generating the dental composite composition. In other embodiments, photopolymerization comprises irradiating at least a portion of the composition with ultraviolet, visible or infrared electromagnetic radiation. In yet other embodiments, the dental composite composition has about twice or higher the service lifetime, or about equivalent or better adhesion performance, or about twice or higher the fatigue performance, or about half or lower the wear/tear performance, and/or about half or less the degradation performance, of a BisGMA/TEGDMA composite.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A: Cu(I) is either directly added or reduced from Cu(II) through reactions with reducing reagents such as sodium ascorbate. FIG. 1B: Cu(I) is generated in situ by radicals upon irradiating photoinitiator and only occurs where and when light irradiates; as a result, crosslinked network are generated via photopolymerization of multifunctional alkynes and azides.

FIGS. 4A-4B illustrate the storage modulus (FIG. 4A) and glass transition temperature, $T_g$ (FIG. 4B), comparison of different polymer networks: CuAAC polymer, synthesized from monomer (1) and (2) (FIG. 3) using the photo-CuAAC, and thiol-Michael polymer, synthesized from trithiol and diacrylate monomers, having the same backbone structures to monomer (1) and (2), using the thiol-Michael addition polymerization reaction.

FIG. 5 illustrates alkyne- and azide-based substrates comprising distinct monomer functionality (n=1-4), cores and linkers. Model compounds comprising varying combinations of the linkers and reactive alkyne or azides are used to assess and determine the most reactive structures. In certain embodiments, the most reactive functional-linker combinations as assessed from monofunctional monomers (n=1) are then attached to the varying core structures to achieve the desired mechanical behavior as dictated by crosslink density, triazole concentration, core stiffness, number and type of alkyne and azide units, and presence and nature of secondary interactions, for example.

DETAILED DESCRIPTION OF THE INVENTION

Figure 1A:
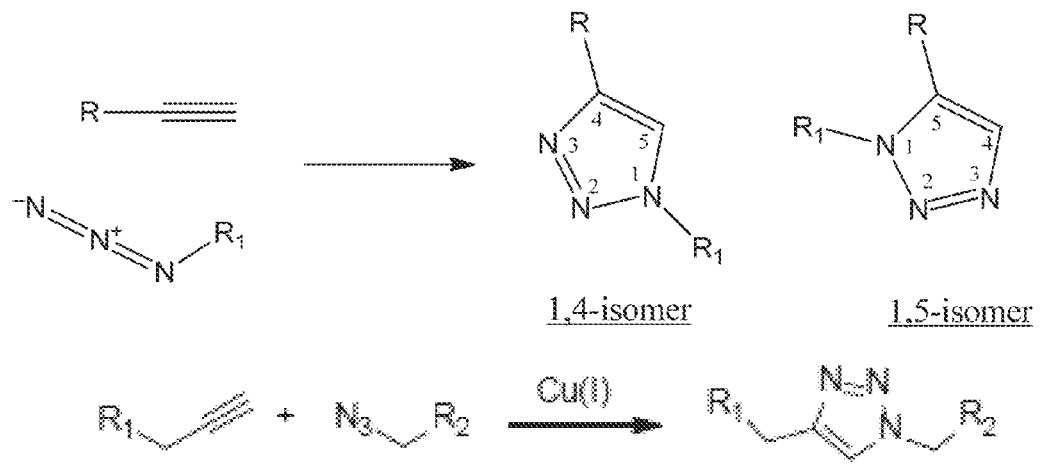
FIGS. 1A-1B illustrate the mechanism of the CuAAC reactions in both (FIG. 1A) conventional coupling of model compounds and (FIG. 1B) photo-initiated reaction of multifunctional monomers to form a crosslinked polymer network based on the CuAAC reaction where "●" in the scheme represents the triazole linkage.

The present invention relates to the unexpected discovery of novel composite compositions based on the CuAAC reaction. This use of the "click" reaction for composite preparation is desirable because this reaction achieves high monomer conversion without side reactions, has robust performance at ambient temperature and forms a product that is not readily degradable. Moreover, the product of the reaction is a triazole ring structure, which is capable of secondary molecular interactions (i.e., non-covalent bond formation) that enhance toughness, glass transition, and modulus of the crosslinked polymer material. Further, as compared to other photopolymerization reactions, this approach has distinct advantages from the dental material perspective: it makes inherently glassy materials, forms those materials via a step-growth reaction that delays gelation and reduces shrinkage stress, and the reaction products are inherently stable.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkyne-based substrate" refers to a small molecule or a polymeric molecule comprising at least one reactive alkynyl group. An "alkynyl group" is an unsaturated, linear or branched or cyclic hydrocarbon group consisting at least one carbon-carbon triple bond. In certain embodiments, the alkyne-based substrate comprises preferably at least one terminal alkynyl group (—C≡CH).

As used herein, the term "azide-based substrate" refers to a small molecule or a polymeric molecule comprising at least one azide group. The substrate contemplated within the invention may comprise a soluble reagent or a solid-immobilized reagent, such as a surface-immobilized reagent.

As used herein, the terms "comprising," "including," "containing" and "characterized by" are exchangeable, inclusive, open-ended and does not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used herein, "consisting of" excludes any element, step, or ingredient not specified in the claim element.

As used herein, "consisting essentially of" does not exclude materials or steps that do not materially affect the basic and novel characteristics of the claim.

As used herein, the term "curable" as applied to a material refers to a material comprising at least one functional group that may undergo polymerization. The curable material may be non-polymerized (i.e., non-cured material), or may be submitted to polymerization conditions (such as chemical reagents or physical conditions) that induce polymerization of at least a fraction of the at least one polymerizable functional group (i.e., partially or fully cured material). In certain embodiments, polymerization or crosslinking of the curable material results in about 100% consumption of the at least one functional group (i.e., fully cured). In other embodiments, polymerization or crosslinking of the curable material results in less than about 100% consumption of the at least one functional group (i.e., partially cured).

As used herein, the term "instructional material" includes a publication, a recording, a diagram, or any other medium of expression that may be used to communicate the usefulness of the compositions and methods of the invention. In some instances, the instructional material may be part of a kit useful for preparing a dental composite. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; or instructions for use of a composition of the invention.

The term "monomer" refers to any discreet chemical compound of any molecular weight.

As used herein, the term "orthogonal," as applied to the conditions required to run at least two distinct chemical reactions, indicates that the conditions used to perform one of the chemical reactions do not significantly affect the ability to perform the subsequent other(s) chemical reaction(s). In a non-limiting example, reactions R1 and R2 may be performed in a system, wherein R1 is run first and R2 is run second; reactions R1 and R2 are performed under "orthogonal" conditions if reaction R1 may be performed in the system under conditions that do not affect the ability to subsequently perform reaction R2 in the system.

As used herein, the term "photoinducible reducing agent" refers to a molecule that generates at least one reducing species upon irradiation of the reducing agent for a given period of time. In certain embodiments, the electromagnetic irradiation comprises ultraviolet, visible or infrared electromagnetic radiation. In other embodiments, the at least one reducing agent is capable of reducing a Cu(II) salt to a Cu(I) species to a given extent, in the given period of time used in the irradiation of the reducing agent. In non-limiting embodiments, the given extent is calculated as the ratio between (i) the amount of the Cu(II) salt in the system that was reduced to a Cu(I) species and (ii) the amount of the Cu(II) salt in the system before reduction.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of the at least one functional group.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "reactive" as applied to azide or alkyne groups indicate that these groups under appropriate conditions may take part in one or more reactions as defined in this application.

As used herein, the term "Type (I) photoinitiator" refers to a compound that undergoes a unimolecular bond cleavage upon irradiation to yield free radicals. Non-limiting examples of Type (I) photoinitiators are benzoin ethers, benzyl ketals, α-dialkoxy-acetophenones, α-hydroxy-alkylphenones, α-amino-alkylphenones and acyl-phosphine oxides. As used herein, the term "Type (II) photoinitiator" refers to a combination of compounds that undergo a bimolecular reaction where the excited state of the photoinitiator interacts with a second molecule (often known as "coinitiator") to generate free radicals.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, particularly ethyl, methyl, isopropyl, isobutyl, n-pentyl, n-hexyl and cyclopropylmethyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$) cycloalkyl, particularly cyclopropyl, cyclobutyl, cyclopentyl and cyclohexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —$CH$=$CH$—$O$—$CH_3$, —$CH$=$CH$—$CH_2$—$OH$, —$CH_2$—$CH$=$N$—$OCH_3$, —$CH$=$CH$—$N(CH_3)$—$CH_3$, and —$CH_2$—$CH$=$CH$=$CH_2$—$SH$.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —$O$—$CH_2$—$CH_2$—$CH_3$, —$CH_2$—$CH_2$—$CH_2$—$OH$, —$CH_2$—$CH_2$—$NH$—$CH_3$, —$CH_2$—$S$—$CH_2$—$CH_3$, and —$CH_2CH_2$—$S$ (=O)—$CH_3$. Up to two heteroatoms may be consecutive, such as, for example, —$CH_2$—$NH$—$OCH_3$, or —$CH_2$—$CH_2$—$S$—$S$—$CH_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl. Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl. The aforementioned listing of heterocyclyl and heteroaryl moieties is intended to be representative and not limiting.

As used herein, the term "substituted" means that an atom or group of atoms has replaced hydrogen as the substituent attached to another group.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —NH$_2$, —N(CH$_3$)$_2$, —C(=O)OH, trifluoromethyl,—C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of C$_{1-6}$ alkyl, —OH, C$_{1-6}$ alkoxy, halo, amino, acetamido and nitro. In yet other embodiments, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one aspect, the present invention relates to the unexpected discovery of novel composite compositions based on the CuAAC reaction. This use of this reaction for composite preparation is desirable because the reaction achieves high monomer conversion without side reactions, has robust performance at ambient temperature and forms a product that is not readily degradable. Moreover, the product of the reaction is a triazole ring structure, which is capable of secondary molecular interactions (i.e., non-covalent bond formation) that enhance toughness, glass transition, and modulus of the crosslinked polymer material. Further, as compared to other photopolymerization reactions, this approach has distinct advantages from the dental materials perspective, such as, but not limited to, it makes inherently glassy materials, forms those materials via a step-growth reaction that delays gelation and reduces shrinkage stress, and the reaction products are inherently stable.

In certain embodiments, the polymerized compositions of the invention comprise one or more of the following characteristics: good mechanical performance (evaluated in terms of modulus, toughness, swelling, low wear and/or long durability); good biological performance (evaluated in terms of biocompatibility, non-toxicity, non-degradability, and/or absence of non-biofilm formation); aesthetics and handling characteristics (evaluated in terms of rheological behavior and appearance), good curing characteristics (evaluated in terms of on-demand curing, rapid reaction, and/or successful curing of thick materials) and others (such as low shrinkage and stress, excellent adhesion to the interface, strong interface between filler and resin, and the like).

In certain embodiments, the compositions of the invention have one or more of the following characteristics: lack of esters and other degradable groups; presence of secondary interactions that strengthen the material; presence of long-lived, non-coupled catalysts that facilitate long-term reaction of thick composites; high conversion of monomers upon polymerization; use of step growth reactions that impart low shrinkage and low stress, and allow for prepolymerization; and compatibility with other dental composites, such as adhesives.

Figure 1B:
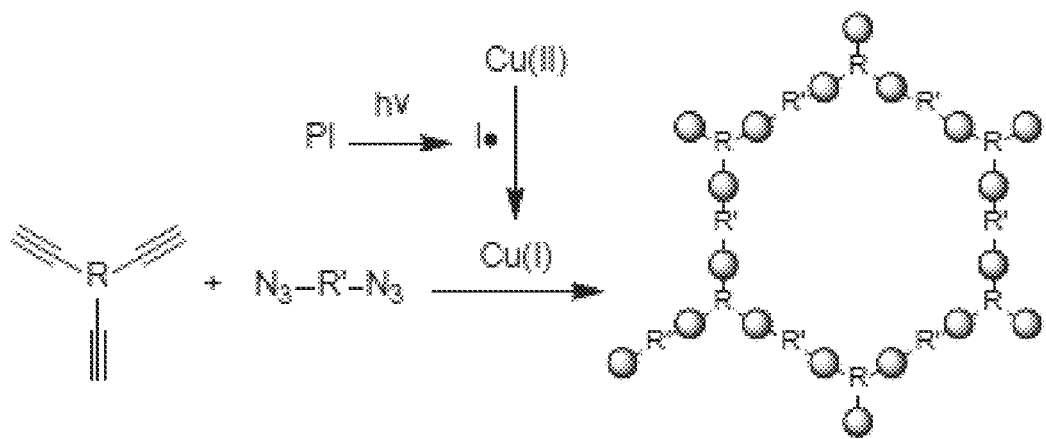

In certain embodiments, to design and develop a novel dental composite restorative system, one must possess a fast kinetic profile with minimal or no side reactions that would adversely affect the network properties. These characteristics are all attributes of the broad class of "click" reactions. The mechanism of the CuAAC reaction itself is presented in FIGS. 1A-1B. Broadly, the cycloaddition reaction between the azide and alkyne species is catalyzed by Cu(I), without which the reaction proceeds approximately seven orders of magnitude more slowly. The Cu(I) species is traditionally generated in bulk via the addition of Cu(II) salts and an appropriate reducing agent such as sodium ascorbate.

In certain embodiments, the compositions of the invention are prepared through the reaction of an alkyne, an azide and copper ions. In other embodiments, the components of the composition of the invention are biocompatible or have minimal and manageable potential for toxicity. Both alkynes and azides are generally considered to be biocompatible materials. Copper is one of the micronutrients that the human body requires on a daily basis, and copper deficiency causes many hematological manifestations, such as myelodysplasia, anemia, leucopenia, and neutropenia. Commercially available daily dose copper supplements contain up to 2 to 3 mg of copper per capsule. In certain embodiments, for a typical dental restorative filling that might consist of hundreds of milligrams of composite, less than a few milligrams of copper catalyst is needed to initiate the polymerization (e.g., there would be 0.3 mg copper catalyst in 100 mg of composite with 70 wt % filler and 1% Cu in the resin phase). Further, the copper species strongly bind to alkyne, amine, and triazole ligands present throughout the network, and thus do not readily escape the composite. In certain embodiments, the CuAAC reaction is biocompatible and achieves the necessary reaction and mechanical behavior while eliminating degradation pathways that reduce the serviceable lifetime of composite restoratives.

Figure 2:
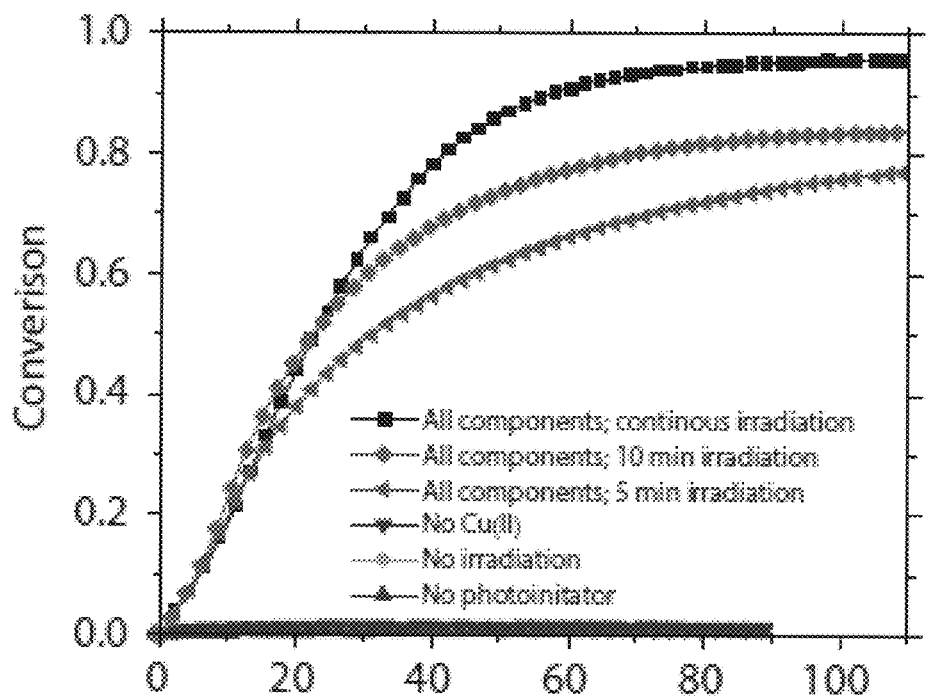
FIG. 2 is a graph illustrating photo-CuAAC reaction kinetics. The complete conversion of the azide species occurred in approximately 1 hour for a DMF solution with 200 mM ethylazidoacetate, 200 mM 1-hexyne, 10 mM copper sulfate, and 10 mM Irgacure 819 irradiated (2.5 mol % for both copper sulfate and I819) with 10 mW/cm$^2$ 400-500 nm light. Also shown is the azide conversion, or lack thereof, for mixtures without Cu(II), irradiation, or photoinitiator. No significant reaction was noted for any of these samples and all three lines overlay. Conversion was also shown when irradiation was ceased after five or ten minutes during the course of the reaction.

In certain embodiments, conventional CuAAC reactions, where the catalytic Cu(I) species is formed by in situ reduction from Cu(II) species using reducing agents, is not easily applicable to dental restorations. The lack of photo-control over the reaction is a primary limitation for on-demand curing. In certain embodiments, the CuAAC reaction may be performed through photoinduction by adding a photoinitiator to the reaction mixture. The resulting photo-generated radicals, formed upon irradiation, reduce Cu(II) to Cu(I) to catalyze the reaction. In certain embodiments, the composition of the invention is stable in the absence of light exposure (Cu(II) does not initiate the reaction) and then readily cures upon exposure to light. In other embodiments, $TiO_2$ and I819 (a visible light phosphine oxide photoinitiator) are effective in catalyzing the CuAAC reaction upon visible light (400-500 nm) irradiation (FIG. 2). In the absence of any of the critical elements (light, radical generator, Cu, and the like), no reaction takes place.

The product of the CuAAC reaction is a 1,2,3-triazole functional group (FIGS. 1A-1B), a rigid aromatic ring structure which is also chemically robust to oxidation, reduction, and hydrolysis. In bulk polymerization, this linkage should lead to a novel type of polymer network with high modulus and glass transition temperature, accompanied by excellent chemical resistance to a variety of environmental conditions and toughening associated with the increased prevalence of secondary interactions between the triazole ring structures.

Overall, the photo-induced CuAAC polymerization system is suited for the next generation of dental restoratives. The reaction is easily controlled by light, and the resulting polymer possesses superior stability towards hydrolysis, oxidation, and reduction because of the aromatic triazole linkage throughout the network, which also promotes high glass transition temperature and high modulus. The polymerization kinetics experiments demonstrate that about 5 minutes of irradiation at much lower than clinical light intensities (about 5 mW/cm$^2$ versus current clinical practice most commonly in the range of 400-600 mW/cm$^2$) is sufficient to achieve a fully cured polymer.

The compositions of the invention offer great advantages over the standard BisGMA-based methacrylate resins of the art. Without wishing to be limited by any theory, for example, a simple calculation (assuming equal reactivity and homogeneity) for the model system at 80% conversion (already achieved at low light intensities) compared to commercial dimethacrylate resins at 70% conversion (generally higher than achieved in practice) would indicate that 9% of the monomers are completely unreacted and available for extraction in the dimethacrylate while less than 3% would be in the model CuAAC system. At 90% conversion in the CuAAC model system, the unreacted monomer would be less than 1%.

In one aspect, the polymerization scheme of the invention makes it possible to completely eliminate ester and other functional groups, eliminating the potential for enzymatic and/or hydrolytic degradation. The ester functionality in the methacrylate is readily degraded under relatively mild conditions, while the potential to form essentially an aliphatic (potentially with some ether or thiocarbamate bonds) triazole polymer would reduce the bond degradation potential by orders of magnitude. Given that multiple bonds have to be degraded to release any reacted component, in certain embodiments, the compositions of the invention dramatically reduce degradation by at least an order of magnitude in mass loss.

In certain embodiments, with respect to the mechanics and long-term mechanical performance, the more hydrophobic CuAAC polymer significantly limits the loss of performance due to swelling and/or degradation in an aqueous environment. Further, the step-growth nature of the polymerization increases the gel point conversion, leading to low shrinkage stress. All of these represent desirable features for dental restorative materials. Without wishing to be limited by any theory, the compositions of the invention may have a service lifetime that is at least twice that of the current dimethacrylate-based composite.

Compositions

In one aspect, the invention includes a composition comprising an alkyne-based substrate and an azide-based substrate. In certain embodiments, the composition is suitable for use in the preparation of dental composites. The alkyne-based substrate contemplated within the invention is a small molecule or a polymeric molecule comprising at least one reactive alkynyl group. In certain embodiments, the alkyne-based substrate comprises at least one terminal alkynyl group. The azide-based substrate contemplated within the invention is a small molecule or a polymeric molecule comprising at least one reactive azide group.

In certain embodiments, the composition comprises at least one compound selected from the group consisting of

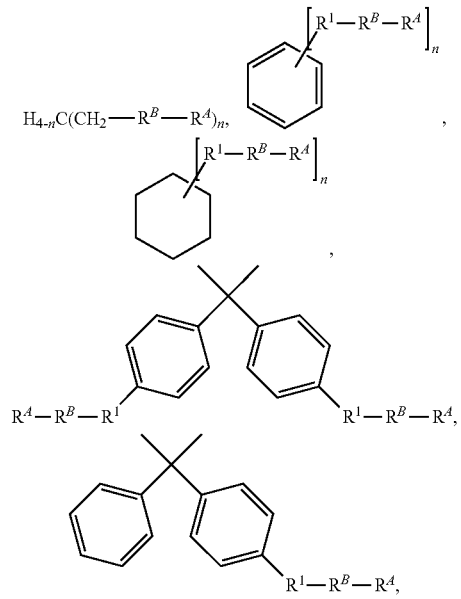

a salt or solvate thereof, and any combinations thereof, wherein: n=1-4; each occurrence of $R^1$ is independently a bond, —$CH_2$—, —O—, or —$NR^2$—; each occurrence of $R^2$ is H or $C_1$-$C_6$ alkyl; each occurrence of $R^B$ is independently $C_1$-$C_6$ alkanediyl, $C_1$-$C_6$ heteroalkanediyl; arenediyl, heteroarenediyl, —$(CH_2)_{0-4}$—NHC(=O)S—$(CH_2)_{0-4}$—, or —$(CH_2)_{0-4}$—SC(=O)NH—$(CH_2)_{0-4}$—; wherein the alkanediyl, heteroalkanediyl, arenediyl and heteroarenediyl groups are optionally and independently substituted with one or more groups selected from the group consisting of OH, F, Cl, Br, I, alkyl, perfluoroalkyl, alkoxy, perfluoroalkoxy, $NH_2$, acylamino, amido, carboxyl, alkoxycarbonyl, acyloxy, formyl, acyl, thioester, carbamate, urea, sulfonate, sulfamoyl, sulfone, sulfonamide, CN, $NO_2$, and alkylthio; and, each occurrence of $R^A$ is independently $N_3$ or —C≡C—H.

In certain embodiments, the $C_1$-$C_6$ alkanediyl comprises methanediyl (methylene), 1,2-ethanediyl, or 1-3-propanediyl. In other embodiments, the heteroalkanediyl comprises —$(CH_2)_{0-4}$—$NR^2$—$(CH_2)_{0-4}$—, —$(CH_2)_{0-4}$—O—$(CH_2)_{0-4}$—or —$(CH_2)_{0-4}$—S—$(CH_2)_{0-4}$—.

In certain embodiments, the molar ratio of the at least one reactive alkyne group and the at least one reactive azide group in the composition is such that polymerization of the composition results in greater than about 80%, or 85%, or 90%, or 95%, or 99%, or 99.9%, or 99.99%, or 99.999% conversion of the alkyne-based substrate and/or the azide-based substrate.

In certain embodiments, the molar ratio of the at least one reactive alkyne group and the at least one reactive azide group in the composition ranges from about 0.5 to about 2. In other embodiments, the molar ratio of the at least one reactive alkyne group and the at least one reactive azide group in the composition ranges from about 0.5 to about 0.75. In yet other embodiments, the molar ratio of the at least one reactive alkyne group and the at least one reactive azide group in the composition ranges from about 0.75 to about 0.85. In yet other embodiments, the molar ratio of the at least one reactive alkyne group and the at least one reactive azide group in the composition ranges from about 0.85 to about 1. In yet other embodiments, the molar ratio of the at least one reactive alkyne group and the at least one reactive azide group in the composition is about 1. In yet other embodiments, the molar ratio of the at least one reactive alkyne group and the at least one reactive azide group in the composition ranges from about 1 to about 1.15. In yet other embodiments, the molar ratio of the at least one reactive alkyne group and the at least one reactive azide group in the composition ranges from about 1.15 to about 1.25. In yet other embodiments, the molar ratio of the at least one reactive alkyne group and the at least one reactive azide group in the composition ranges from about 1.25 to about 1.5.

In certain embodiments, the composition further comprises at least one Cu(II) salt. In other embodiments, the composition further comprises at least one photoinducible reducing agent. In yet other embodiments, the at least one photoinducible reducing agent is a Type (I) photoinitiator.

The at least one Cu(II) salt contemplated within the invention comprises a copper(II)-containing salt, such as, but not limited to, copper(II) sulfate, copper(II) chloride, copper(II) bromide, copper(II) iodide, copper(II) perchlorate, copper(II) nitrate, copper(II) hydroxide, copper(II) oxide, and hydrates and mixtures thereof. Non-limiting examples of hydrates are copper(II) sulfate pentahydrate, copper(II) nitrate hydrate, copper(II) nitrate.$2.5H_2O$, copper (II) perchlorate hexahydrate, copper(II) chloride dihydrate and the like.

The at least one photoinducible reducing agent contemplated within the invention is a molecule that generates at least one reducing species upon irradiation of the reducing agent with a given wavelength at a given intensity for a given period of time. A radical photoinitiator known in the art may be employed, such as benzoin ethers and phenone derivatives such as benzophenone or diethoxyacetophenone.

Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In certain embodiments, the UV light source emits light between about 350 nm and about 400 nm. In some embodiments, the UV light source emits light between about 400 nm and about 500 nm.

In certain embodiments, the irradiation comprises ultraviolet electromagnetic radiation, visible electromagnetic radiation or infrared electromagnetic radiation. In other embodiments, the electromagnetic radiation comprises ultraviolet or visible electromagnetic radiation.

In certain embodiments, the free radical initiated photopolymerization is photoinitiated by any light wavelength range within the ultraviolet (about 200 to about 400 nm) and/or visible light spectrum (about 380 to about 780 nm). The choice of the wavelength range can be determined by the photoinitiator employed. In certain embodiments, a full spectrum light source, e.g. a quartz-halogen xenon bulb, may be utilized for photopolymerization. In other embodiments, a wavelength range of about 320 to about 500 nm is employed for photopolymerization.

In certain embodiments, the at least one reducing agent is capable of reducing the at least one Cu(II) salt of the composition to a given extent to a Cu(I) species, upon irradiation of the composition for the given period of time. In other embodiments, the given extent is from about 0.01% to about 5%. In yet other embodiments, the given extent is from about 5% to about 10%. In yet other embodiments, the given extent is from about 10% to about 25%. In yet other embodiments, the given extent is from about 25% to about 50%. In yet other embodiments, the given extent is from about 50% to about 75%. In other embodiments, the given extent is from about 75% to about 100%.

Non-limiting examples of the at least one reducing agent contemplated within the invention are: 1-hydroxy-cyclohexyl-phenyl-ketone (Irgacure 184; Ciba, Hawthorne, N.J.); a 1:1 mixture of 1-hydroxy-cyclohexyl-phenyl-ketone and benzophenone (Irgacure 500; Ciba, Hawthorne, N.J.); 2-hydroxy-2-methyl-1-phenyl-1-propanone (Darocur™ 1173; Ciba, Hawthorne, N.J.); 2-hydroxy-1-[4-(2-hydroxyethoxyl) phenyl]-2-methyl-1-propanone (Irgacure 2959; Ciba, Hawthorne, N.J.); methyl benzoylformate (Darocur™ MBF; Ciba, Hawthorne, N.J.); oxy-phenyl-acetic acid 2-[2-oxo-2-phenyl-acetoxy-ethoxy]-ethyl ester; oxy-phenyl-acetic 2-[2-hydroxy-ethoxy]-ethyl ester; a mixture of oxy-phenyl-acetic acid 2-[2-oxo-2-phenyl-acetoxy-ethoxy]-ethyl ester and oxy-phenyl-acetic 2-[2-hydroxy-ethoxy]-ethyl ester (Irgacure 754; Ciba, Hawthorne, N.J.); alpha,alpha-dimethoxy-alpha-phenylacetophenone (Irgacure 651; Ciba, Hawthorne, N.J.); 2-benzyl-2-(dimethylamino)-1-[4-(4-morpholinyl)-phenyl]-1-butanone (Irgacure 369; Ciba, Hawthorne, N.J.); 2-methyl-1-[4-(methylthio)phenyl]-2-(4-morpholinyl)-1- propanone (Irgacure 907; Ciba, Hawthorne, N.J.); a 3:7 mixture of 2-benzyl-2-(dimethylamino)-1-[4-(4-morpholinyl)phenyl]-1-butanone and alpha,alpha-dimethoxy-alpha-phenylacetophenone per weight (Irgacure 1300; Ciba, Hawthorne, N.J.); diphenyl-(2,4,6-trimethylbenzoyl) phosphine oxide (Darocur™ TPO; Ciba, Hawthorne, N.J.); a 1:1 mixture of diphenyl-(2,4,6-trimethylbenzoyl)-phosphine oxide and 2-hydroxy-2-methyl-1-phenyl-1-propanone (Darocur™ 4265; Ciba, Hawthorne, N.J.); phenyl bis(2,4,6-trimethyl benzoyl) phosphine oxide, which may be used in pure form (Irgacure 819; Ciba, Hawthorne, N.J.) or dispersed in water (45% active, Irgacure 819DW; Ciba, Hawthorne, N.J.); a 2:8 mixture of phosphine oxide, phenyl bis(2,4,6-trimethyl benzoyl) and 2-hydroxy-2-methyl-1-phenyl-1-propanone (Irgacure 2022; Ciba, Hawthorne, N.J.); Irgacure 2100, which comprises phenyl-bis(2,4,6-trimethylbenzoyl)-phosphine oxide); bis-(eta 5-2,4-cyclopentadien-1-yl)-bis-[2,6-difluoro-3-(1H-pyrrol-1-yl)phenyl]-titanium (Irgacure 784; Ciba, Hawthorne, N.J.); (4-methylphenyl) [4-(2-methylpropyl)phenyl]-iodonium hexafluorophosphate (Irgacure 250; Ciba, Hawthorne, N.J.); 2-(4-methylbenzyl)-2-(dimethylamino)-1-(4-morpholinophenyl)-butan-1-one (Irgacure 379; Ciba, Hawthorne, N.J.); 4-(2-hydroxyethoxy)phenyl-(2-hydroxy-2-propyl)ketone (Irgacure 2959; Ciba, Hawthorne, N.J.); bis-(2,6-dimethoxybenzoyl)-2,4,4-trimethylpentylphosphine oxide; a mixture of bis-(2,6-dimethoxybenzoyl)-2,4,4-trimethylpentylphosphine oxide and 2-hydroxy-2-methyl-1-phenyl-propanone (Irgacure 1700; Ciba, Hawthorne, N.J.); acyl germane photonitiators (such as $Et_2Ge(C(=O)Ph)_2$); titanium dioxide; camphorquinone/amine systems; primary amines (such as, but not limited to, alkylamines, arylalkylamines or heteroarylalkylamines, which form reducing systems in the presence of Cu(II) and appropriate radiation); and mixtures thereof.

The at least one reducing agent may be used in amounts ranging from about 0.01 to about 25 weight percent (wt %) of the composition, more preferably from about 0.1 to about 20 wt % of the composition, more preferably from about 1 to about 15 wt % of the composition, more preferably from about 2 to about 10 wt % of the composition.

The at least one Cu(II) salt may be used in amounts in which the ranging from about 0.01 to about 25 wt % of the composition, more preferably from about 0.1 to about 20 wt % of the composition, more preferably from about 1 to about 15 wt % of the composition, more preferably from about 2 to about 10 wt % of the composition.

In certain embodiments, the composition further comprises a Cu(I)-stabilizing ligand. In other embodiments, the Cu(I)-stabilizing ligand comprises a tertiary amine. In other embodiments, the Cu(I)-stabilizing ligand comprises at least one selected from the group consisting of TBTA (tris[(1-benzyl-1H-1,2,3-triazol-4-yl)methyl]amine); BTTES (2-4-(bis1-tert-butyl-1H-1,2,3-triazol-4yl)methylamino(methyl-1H-1,2,3-triazol-1-yl)ethanesulfonic acid); $N^1$-(2-(dimethylamino)ethyl)-$N^1,N^2,N^2$-trimethylethane-1,2-diamine; $N^1,N^2$-(ethane-1,2-diyl)bis($N^1,N^2,N^2$-trimethylethane-1,2-diamine); 2,2'-bipyridine and any combinations thereof.

In certain embodiments, the composition further comprises a filler, a bonding agents and/or a coupling agent. In certain embodiments, functionalized fillers are incorporated into the composite compositions of the invention to optimize their performance as dental composite systems. Non-limiting examples of fillers include inorganic filler compounds such as titanium dioxide, barium, ytterbium, strontium, zirconia silicate, or amorphous silica.

In certain embodiments, the inclusion of fillers in the compositions of the invention improves their mechanical performance and reduces shrinkage, stress and moisture uptake. Fillers generally enhance the hardness of the materials while also imparting increased wear resistance and reducing polymerization shrinkage. Most importantly, the nature, type, size distribution, and surface modification of the filler significantly contribute to the integration of the filler within the resin as necessary to improve the overall mechanical strength and function of the dental composite over its life cycle. In certain embodiments, the filler is used to modulate the viscosity, hydrophilicity and stiffness (rubbery modulus) of the unpolymerized or polymerized composition.

In certain embodiments, the composition further comprises a filler. In other embodiments, the filler comprises an alkyne-functionalized particle. In other embodiments, the filler comprises an azide-functionalized particle. In other embodiments, the filler comprises an alkyne-functionalized particle and an azide-functionalized particle. In yet other embodiments, the functionalized particle further comprises silica or titanium dioxide.

A nanoparticle is defined as any particle less than 100 nanometers (nm) in diameter. A nanocluster is an agglomeration of nanoparticles. In certain embodiments, utilization of nanoclusters in a nanosized filler can be exploited to increase the load and improve some mechanical properties. Other suitable fillers are known in the art, and include those that are capable of being covalently bonded to the impression material itself or to a coupling agent that is covalently bonded to both. Examples of suitable filling materials include but are not limited to, barium glass, ytterbium nanoglasses and nanoclusters, fumed silica, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Some of the aforementioned inorganic filling materials and methods of preparation thereof are disclosed in U.S. Pat. Nos. 4,544,359 and 4,547,531; pertinent portions of each of which are incorporated herein by reference.

The filler may be silanized and typically presented in the form of particles with a size ranging from 0.01 to 5.0 micrometers. In certain embodiments, the filler is a hydrophobic fumed silica. In other embodiments, the hydrophobic fumed silica filler is composed of nanoparticles or nanoclusters. In yet other embodiments, the filler is a mixture of barium glass, ytterbium nanoglasses and nanoclusters, and fumed silica. In yet other embodiments, the filler is 85 wt % 0.5 micron barium glass, 10 wt % ytterbium 40 nm nanoglass and nanoclusters, 2.5 wt % Aerosil fumed silica, and 2.5 wt % Cabosil fumed silica. In other embodiments, the filler is a mixture of 90% 0.4 µm Schott glass and 10 wt % Aerosol OX-50. The filler materials may be combined with the resins of the disclosure to form a dental composite material with high strength along with other beneficial physical and chemical properties.

In certain embodiments, suitable fillers are those having a particle size in the range from about 0.01 to about 5.0 micrometers, mixed with a silicate colloid of about 0.001 to about 0.07 micrometers. The filler may be utilized in the filled resin compositions of the disclosure in the amount of from about 40 wt % to about 90 wt %; preferably about 60 wt % to 85 wt %; more preferably about 70 wt % to about 80 wt % of the total weight of the composition. In one specific embodiment, 72.5 wt % filler is utilized in the filled resin composition. In another specific embodiment, 60 wt % filler is utilized in the filled resin composition.

In certain embodiments, the composition further comprises a dimethacrylate monomer. In other embodiments, the dimethacrylate monomer comprises bisphenol A dimethacrylate (BisGMA) or triethyleneglycol dimethacrylate (TEGMA).

In certain embodiments, the composition further comprises a compatibilizer. In other embodiments, the compatibilizer comprises an alkynyl group and an alkenyl group. In yet other embodiments, the compatibilizer is selected from the group consisting of prop-2-yn-1-yl methacrylate, prop-2-yn-1-yl acrylate, N-(prop-2-yn-1-yl)methacrylamide, N-(prop-2-yn-1-yl) acrylamide, N-methyl-N-(prop-2-yn-1-yl)methacrylamide, N-methyl-N-(prop-2-yn-1-yl) acrylamide, and any combinations thereof.

In certain embodiments, the resin composition further comprises a polymerization inhibitor, or stabilizer. Examples of inhibitors include hydroquinone monomethyl ether (MEHQ), aluminum-N-nitrosophenylhydroxylamine, and 2,6-di-tertbutyl-4-methylphenol (BHT). In certain embodiments, the inhibitor is aluminum-N-nitrosophenylhydroxylamine (Q1301, Wako Pure Chemical, Osaka, Japan). The optional inhibitor may be utilized in the amount of from about 0.001 wt % to about 0.5 wt %, or about 0.01 wt % to about 0.1 wt % of the resin composition. In certain embodiments, the inhibitor aluminum-N-nitrosophenyl-hydroxylamine is utilized as 0.035 wt % of the resin. In other embodiments, aluminum-N-nitrosophenylhydroxylamine is utilized at 0.075 wt % of the total weight of the filled resin composition.

Methods

In one aspect, the invention includes a method of preparing a dental composite composition.

In certain embodiments, the method comprises photopolymerizing at least a portion of an at least partially unpolymerized composition of the invention, thereby generating the dental composite composition. In other embodiments, photopolymerization of the substrates comprises irradiating at least a portion of the composition with ultraviolet, visible or infrared electromagnetic radiation. In yet other embodiments, the dental composite composition of the invention has about twice or higher the service lifetime, and/or about equivalent or better adhesion performance, and/or about twice or higher the fatigue performance, and/or about half or lower the wear/tear performance, and/or about half or less the degradation performance of a BisGMA/TEGDMA composite.

Kits

The invention includes a kit relating to the compositions and methods of the invention. Although exemplary kits are described below, the contents of other useful kits will be apparent to the skilled artisan in light of the present disclosure. Each of these kits is included within the invention. The kits of the present invention are useful, because, as disclosed elsewhere herein, such kits can be used to prepare composite compositions that are useful as parts of dental implants.

The kit of the present invention may comprise the reagents necessary to set up a photoinduced "click" reaction between an alkyne-based substrate and an azide-based substrate. The kit of the present invention may further comprise components that allow the modification of a solid surface, so that the products of the photoinduced "click" reaction are covalently bound to solid surface.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Unless described otherwise, the materials used in the experiments were obtained from commercial sources or obtained by methods known in the art, and used without further purification.

Example 1

Figure 3:
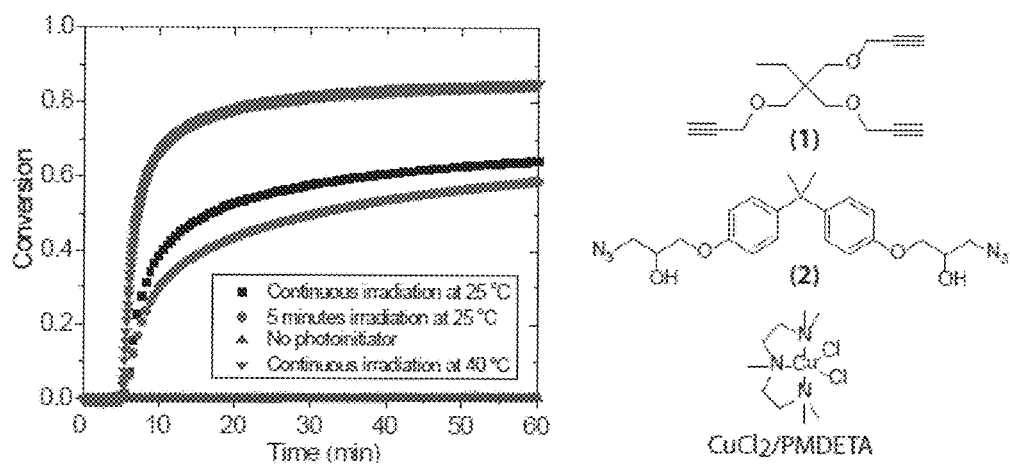
FIG. 3 illustrates the bulk photo-CuAAC polymerization kinetics. High conversion (83%) of the azide species occurred in 1 hour for a mixture of tris(propargyl methoxy) butane (1), bisphenol A di(3-azido-2-hydroxypropan-1-ol) ether (2), 1 mol % of CuCl$_2$/PMDETA (pentamethyldiethylenetriamine) and bis-(2,4,6-trimethylbenzoyl)-henylphosphineoxide (I819) irradiated at 40° C. starting after 5 min in the dark with 5 mW/cm$^2$ of 400-500 nm light. The azide conversion for light-exposed mixtures without photoinitiator exhibited no reaction. Also shown are conversion for 5 min and continuous irradiation at 25° C.

The photo-CuAAC reaction was explored in bulk photopolymerizations. Various multifunctional alkyne and azide monomers were synthesized and mixed with a photoinitiator (I819 in this case) and Cu(II) complex (FIG. 3, right). Upon irradiation with 400-500 nm light, the photoinitiator generated radicals that reduce Cu(II) to Cu(I) in situ, thus triggering the CuAAC reaction. The CuAAC photopolymerization was monitored using real-time FTIR.

There was no significant azide conversion for the first 5 minutes before irradiation begins. Despite using only low intensities (5 mW/cm$^2$), there was a rapid conversion of azide in the first 5 minutes. In the later stages of the reaction the conversion reached a plateau near 70% azide conversion at ambient temperature. At slightly higher temperatures (40° C.) the same polymerization reached over 70% conversion in less than 5 minutes. This result showed the temporal control of the reaction and the rapid formation of a crosslinked, high $T_g$ polymer at mild photoinitiation conditions. As in the previous photo-CuAAC polymerization, both the Cu(II) species and photoinitiators were necessary to initiate the reaction, additionally supporting the in situ Cu(I) generation via radical reduction mechanism shown in FIG. 1B.

In certain embodiments, the bulk photo-CuAAC reaction, only an initial dose of light is necessary to initiate the reaction, which remains active for an extended period and achieves even higher conversions in the dark. Without wishing to be limited by any theory, the dark polymerization, in stark contrast to the relatively minimal dark polymerization in radical-mediated polymerizations, arises because of the persistence of the in situ generated Cu(I)

species. Unlike radicals, which if provided sufficient mobility (which is also necessary for propagation and continued polymerization), continue to polymerize only for a very short time, the Cu(I) catalyst may have a lifetime of hours to days in its mobile state, depending on the conditions. In certain embodiments, the extended dark reaction time minimizes the effects of vitrification and enables the achievement of an even higher conversion, lower extractables, and greater depth of cure.

Example 2

FIGS. 4A-4B illustrate the temperature dependent modulus of the crosslinked CuAAC-based polymer as determined by dynamic mechanic analysis (DMA). The polymer was synthesized using the photo-CuAAC methodology from the model resin, monomer (1) and (2) in FIG. 3. A thiol-acrylate polymer is shown as a comparison that has a similar crosslink density but a much more flexible backbone as compared to the triazoles.

The triazole presence had a dramatic effect on the $T_g$, achieving a $T_g$ of 118° C. in comparison to the 45° C. $T_g$ of the non-triazole containing polymer. The glass transition temperature of the CuAAC polymer remained the same after 6 months of storage, and there was no other evidence of any change in material properties over this time.

The volumetric shrinkage behavior during the photo-CuAAC reaction was measured using monomer (2) in FIGS. 3 and 4-pentyl-1-ol in chloroform (molar ratio of azide/alkyne to $CuCl_2$/PMDETA/I819 as 50:50:1:1, the same as the bulk model system). This revealed a 22.2 ml/mol molar volume change per triazole formed, which is similar to the 22.6 ml/mol molar volume change per double bond for the commercially available BisGMA/TEGDMA dental restorative system. In certain embodiments, the total shrinkage is lower in the CuAAC polymerization because the formed triazole concentration is less than the required methacrylate concentration. With appropriate fillers, the composite shrinkage may be reduced further. The preliminary shrinkage induced stress measurements performed using a tensometer on the bulk system (monomers in FIG. 3) exhibited an extremely low stress around 0.2 MPa, which is an order of magnitude less than the BisGMA/TEGMA control, which has a final stress value above 2 MPa under the same conditions.

Example 3

Multifunctional azide and alkyne monomers, as well as suitable visible light initiating systems, are investigated as components of the CuAAC-based photopolymerization reaction. In certain embodiments, results obtained herein allow for identification of a system with reaction kinetics and mechanical property performance that meet or exceed that of the control BisGMA/TEGDMA resin system.

In certain embodiments, the experiments described herein allow one to achieve at least one of the following objectives: identify alkyne and azide monomers of varying functional groups and core structures that form polymerizable monomer mixtures (i.e. the resin); identify a visible light initiating system to enable deep cure; achieve rapid polymerization kinetics with high monomer conversion and low amounts of extractables; and achieve a high glass transition temperature, high modulus, tough polymer network with low volumetric shrinkage and induced shrinkage stress. The photoinitiated CuAAC reaction is a valid dental restorative approach based on the ability to have high $T_g$, tough polymers formed from a step growth reaction that leads to stable polymer structures. In certain embodiments, described herein a non-limiting examples of approaches to evaluate and improve the reaction kinetics and mechanical performance of the photo-CuAAC resin.

For the reaction kinetics and conversion measurements, FTIR is used to monitor both the alkyne and azide group conversion (mid-IR measurements for thin film polymerization and any solution reactions, and near-IR measurements for bulk polymerization of thick samples) at various reaction conditions (temperature, light intensity, monomer, and photoinitiator concentration, and the like). Unless otherwise noted, stoichiometric mixtures of alkyne and azide monomers are formulated with 1wt % each of $CuCl_2$/PMDETA and I819 (a phosphine oxide based visible light radical initiator) and exposed to 10 $mW/cm^2$ light in a wavelength range from 400-500 nm. Higher intensities are used to assess clinically relevant timescales and dependence of polymerization rate and final conversion on intensity. Polymerizations are performed at ambient temperature and 35° C. Depth of cure measurements are performed according to ISO 4049.

Modulus, strength, and $T_g$ are measured utilizing DMA and a Materials Testing System (MTS) according to procedures known in the literature. Infrared-based azide and alkyne (and methacrylate for control resins) conversion measurements are used for in situ monitoring of the polymerization kinetics as well as to verify the reacted state of all samples used for mechanical or other property evaluations. Volume shrinkage are measured using a linometer, while stress measurements are performed on a tensometer. In certain embodiments, shrinkage and stress are lower than the control, and shrinkage is below the target 3-8% in resins and 2-4% in the composites. Extractable measurements are made on these resins as described in detail elsewhere herein.

To improve the kinetics and determine the most reactive alkyne and azide functional groups for the photo-CuAAC reaction, a series of photo-CuAAC reactions using model alkynes and azides are performed to determine the most reactive functional group structures. Aliphatic alkynes and azides, aromatic alkynes and azides, and alkynes and azides with different electron densities around the functional groups (given as linkage B variations in FIG. 5) are investigated. The photo-CuAAC experiment of 1-hexyne and ethylazidoacetate in solution (FIGS. 1A-1B) is used as a control to evaluate the reaction kinetics of different alkynes and azides at the same conditions (i.e., same concentration of reagents, same light intensity, same reaction temperature, and the like).

To enhance the mechanical properties and the kinetics, the effect of thiocarbamate (FIG. 5) moieties on kinetics, mechanical performance, degradation and lifetime are determined. Thiocarbamate structures are formed by the simple reaction of a thiol with an isocyanate and are readily incorporated into the proposed alkyne and azide monomers. The thiocarbamate structure is an analogue to the urethane structure in that it has been demonstrated to yield tougher materials with extensive secondary interactions and hydrogen bonding; however, the replacement of the oxygen with sulfur alters the thiocarbamate degradation. In particular, propargyl isocyanates are readily made in a single step and then can be immediately used by reacting such compounds with multifunctional thiols via thiol-isocyanate "click" reaction as a means for generating thiocarbamate containing multifunctional alkynes.

The effect of the catalyst/photoinitiation system on the overall reaction kinetics is also analyzed based on different copper (II) complexes. Ligands are known to affect reaction rates of classic CuAAC reactions. Both $Cu_2SO_4$ in solution and $CuCl_2$/PMDETA in bulk polymerization exhibit reasonable reaction kinetics. However, the effect of specific ligands on the photo-CuAAC reaction is largely unknown. Therefore, several other copper complexes are synthesized and evaluated with respect to their photo-CuAAC catalytic activity. Without wishing to be limited by any theory, amine ligands significantly increase the solubility of the Cu(II) complex and several amine ligands (i.e., aliphatic, aromatic, primary, secondary, tertiary) are selected to react with $CuCl_2$, $CuBr_2$, and other commercially available inorganic Cu(II) salts to form an array of soluble Cu(II) complexes. These Cu(II) complexes are tested in non-polymerizing model systems to identify the Cu(II) complex with the fastest kinetics. These complexes are utilized and assessed in bulk polymerizing systems suitable for dental restorations. In certain embodiments, Cu(II)/amine complex in living cells at low concentration are nontoxic and biocompatible. In other embodiments, amine ligands that further incorporate alkyne or triazole functionalities are covalently coupled to the network during curing and become unextractable.

In certain embodiments, to achieve deep cure, visible light irradiation is used in dental restorations. I819 (a visible light photoinitiator) successfully cures several millimeter thick samples. The camphorquinone/amine system, commonly used in commercial dental restoratives, and $TiO_2$ are also evaluated in photo-CuAAC polymerization reactions.

In certain embodiments, based on the outcome of the reaction kinetics model compound studies, azide and alkyne functional groups with the fastest reaction kinetics with target monomers, polymerizing at least as rapidly as the BisGMA/TEGDMA control resin under similar irradiance conditions, may be identified. After successfully achieving a model system that demonstrates rapid polymerization kinetics and high monomer conversion at body temperature, systematic evaluation of the effects of the core monomer structures and number of functional groups is performed to enhance the mechanical properties. In particular, a high glass transition temperature, modulus, and flexural strength along with low volumetric shrinkage, stress, moisture uptake, degradation and extractables (all as compared to the BisGMA/TEGDMA control) are targeted and achieved by optimizing the monomer structures. FIG. 5 illustrates several non-limiting core structures, each of which can be derivatized with varying numbers of alkyne or azide functional groups of the chemistry identified in the kinetics study. By systematically changing the core and functionality of both the azide and the alkyne, mechanical properties of the formulation are enhanced, and the shrinkage, moisture uptake, and crosslink density are controlled. This allows for the identification of a resin with improved material and lifetime performance characteristics.

In certain embodiments, the monomer structures are designed to assure miscibility, and the structures can be altered to prevent crystallization and reduce viscosity as needed. In other embodiments, the low molecular weight materials reduce the likelihood of viscosity problems, and most of the secondary interactions that would otherwise increase viscosity (such as the thiocarbamate structures) arise only after polymerization. In yet other embodiments, to ensure that conversions are quantitative even in presence of vitrification, monomers may be oligomerized prior to formulation. This oligomerization, readily possible for step growth reactions, decreases the extractable level at otherwise identical conversions and also significantly reduces the shrinkage.

Example 4

Incorporation of a filler system modified by azide and/or alkyne functional groups pendant to the surface into the CuAAC resin system is investigated, such that the filler copolymerizes with the resin to assure appropriate coupling between the filler and resin in the composite.

In certain embodiments, inorganic fillers are integrated into the photoactive resins of the invention, thus enhancing their mechanical properties and wear resistance. The filler significantly affects the properties of the composite both in its pre- and post-cure state. Commercial composites utilize a range of filler types, sizes, and concentrations to optimize performance, but there are several universal concepts; in particular, the composite must have effective chemical integration between the resin and inorganic phase. This outcome is typically achieved by functionalizing the filler surface and/or having a functional silane component within the formulation. Methacrylate species necessarily contain an ester linkage, which is susceptible to hydrolytic degradation. In certain embodiments, functionalization of the filler improves chemical integration between the resin and inorganic phase. In other embodiments, functionalization of the filler enhances the mechanical properties of the composite and reduces hydrolytic and enzymatic degradation at the filler-resin interface.

Filler functionalization:

Silica filler. Dental composites employ a range of filler types, sizes, and concentrations. In certain embodiments, a filler mixture consisting of 90 wt % 0.4 μm glass (Schott) and 10 wt % Aerosil OX50 (nominal size of 40 nm) is used. This mixture is an approximation to commercially viable composites and is utilized in the experimental systems as well as the BisGMA/TEGDMA controls. The effect of filler functionalization is assessed in terms of filler concentration and functionalization. Specifically, fillers are modified with chloro- and trialkoxy-silane azide or alkyne species (FIG. 6) to facilitate chemical incorporation into the azide-alkyne polymerization.

In a non-limiting examples, the functionalization reaction is performed by refluxing the alkoxysilane and silica (after sonication) in toluene, promoting high conversion via the removal of the condensate. The silanated silica is then dried at 80° C. under vacuum for 20 hours. The functionalization is assessed using thermogravimetric analysis (TGA). In a typical experiment, the material undergoes a thermal program from 25 to 800° C. at 10° C./min.

Figure 6:
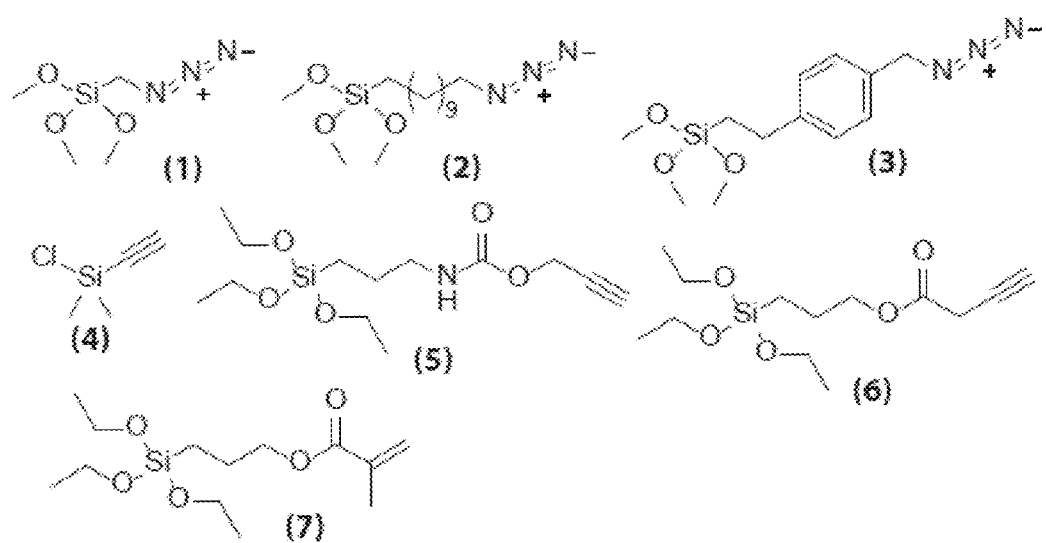
FIG. 6 illustrates azide-containing silane agents (1)-(3), alkyne-containing silane agents (4)-(6) and methacrylate-containing silane agents (7) used to modify the filler. Alkyne structure (4) has no hydrolyzable groups. Alkyne structures (5) and (6) have an urethane group and an ester group, respectively. Structure (7) contains both a methacrylate and an ester groups.

All but the last two species shown in FIG. 6 contain an azide or alkyne functional group and do not contain a hydrolysable ester. Fillers modified with these species provide information on how linkers affect mechanical properties and degradation. Modifiers possessing a carbamate linkage (5) or an ester linkage (6) allow for evaluating degradation stability of functionalized fillers comprising carbamate or ester linkages, respectively. Filler modified with a methacrylate-based trialkoxysilane (7) is used in the control composite formulation (i.e., the BisGMA/TEGDMA system). This latter filler may also be used in an azide-alkyne-based resin to test the null case of the primary hypothesis and assess degradation differences between the different filler functionalized materials.

$TiO_2$ Filler. Photo-activity of $TiO_2$ makes the filler an active component of the dental composite, where the reduction of copper emanates from the surface of the filler. In certain embodiments, $TiO_2$ nanoparticles are used as filler, with the unique property of being able to reduce other species upon the application of light, and further having antimicrobial activities upon irradiation. TiO$_2$ increased hardness and flexural strength of dental implants, as compared with the unaltered control.

In certain embodiments, irradiation of TiO$_2$ leads to the reduction of Cu(II) to Cu(I), thereby initiating polymerization. In other embodiments, TiO$_2$ may be functionalized with trialkoxysilanes as described elsewhere herein.

Formulation. The initial composite composition incorporates a stoichiometric (based on equal alkyne and azide functional group concentrations) balance of monomers 1 and 2 (from FIG. 3), and 1 wt % of both CuCl$_2$-PMDETA and Irgacure 819. The compositions of the invention are compared against a traditional composite control containing 70/30 BisGMA/TEGMA with 1 wt % of Irgacure 819 in the resin phase with methacrylated fillers. In certain embodiments, the functionalized fillers described elsewhere herein are incorporated into the resin at concentrations ranging from about 25% to about 80% using a FlackTek Speed-Mixer.

Composite Evaluation:

In many novel resin systems, the viscosities are too high to incorporate the targeted filler amount. In certain embodiments, the low viscosity of photo-CuAAC monomer resins of the invention is advantageous. In other embodiments, composite compositions of the invention are formulated to the same consistency. The consistency is maintained identical by adding sufficient filler such that placing a 3.5 kg weight on a sample of consistent size (1.0±0.2 cm) for 3 min produces a flattened sample with a diameter of 31 mm. To maintain this consistency, the fractional filler loading may vary slightly for the different resin systems due to differences in resin viscosity as well as the interaction between the resin and filler. The polymerization kinetics (FTIR), mechanical properties (modulus, T$_g$, strength, etc.), volume shrinkage and stress are evaluated on all composites formulations. Mechanical properties are evaluated for the composite compositions of the invention, many of which have become standardized within ISO 4049, which is specific to dental materials. Depth of cure, water sorption and solubility and flexural strength measurements are performed largely according to ISO 4049. In certain embodiments, modifications to the sorption and solubility method are made to include additional environmental effects and longer term studies for many of these measures. Without wishing to be limited by any theory, while no in vitro model fully captures the in vivo environment, subtle modifications allow one to isolate various effects in the oral environment and use them as feedback to redesign and optimize (via synthesis and formulation) the composite system.

Fracture toughness experiments are important, as this property is correlated to the ability of the polymeric materials to resist crack propagation. The fracture toughness is measured by the single-edge notch method using a razor blade insert to create a sharp notch in the specimen. An MTS universal testing machine, in three-point bending mode, is used to fracture the materials (ASTM Standard E399-90, 1997). A Teflon mold is used to make the specimen with the single-edge notch. The 3-point bending test is conducted on an MTS 858 Mini Bionix system. As with other mechanical property measurements, near IR monitoring of the conversion and cure profile is also performed on samples prepared for this technique.

All composite compositions are examined using microscopy, including a focused ion beam-scanning electron microscope (FIB-SEM), to assess the filler stability and distribution. In certain embodiments, a 3D distribution of filler particles is assessed. Such information allows one to understand how the filler interacts with the resin and how this leads to the measured mechanical properties. Moreover, post-fracture examination of the composite provides insight on how filler functionalization affected distribution and ultimately failure.

Example 5

In certain embodiments, compositions of the invention are modified to achieve appropriate integration and adhesion with conventional adhesive systems. In other embodiments, the long-term performance (wear and fatigue behavior) of compositions of the invention are evaluated to demonstrate service lifetimes of at least 2-fold compared to control BisGMA/TEGDMA systems. In yet other embodiments, biocompatibility of compositions of the invention are evaluated to demonstrate at least 2-fold reductions in degradation and extraction products compared to control BisGMA/TEGDMA systems of these CuAAC-based composites.

The formulation of CuAAC-polymerizable azide/alkyne resins into a photocurable composite represents a novel approach to the development of new dental restorative materials. Dental restoratives are known to be susceptible to hygroscopic and hydrolytic effects that result in release of unreacted extractable components as well as degradation products. Release depends on the chemistry, structure, and functional group conversion of the materials, and its effects on material performance and the body are largely unknown though reduced lifetimes and immune responses have been observed. Recurrent caries is the most common reason for replacement of dental restorative materials, and accelerated bacterial growth promoted by extractable and degradation products has been implicated in those caries. Restoration degradation can occur via dissolution, hydrolysis, and wear and erosion from chewing or grinding. In vitro testing is not a perfect mimic for in vivo performance; however, it does serve as a practical screening and ranking tool for composite evaluation. Hydrolysis can be simulated in vitro through appropriate aqueous, salivary, enzymatic, and pH environments.

As noted elsewhere herein, methacrylates necessarily contain esters, which are susceptible to hydrolytic and enzymatic degradation. The novel alkyne/azide resins and functionalized fillers lead to an overall composite system without hydrolysable groups and with only stable chemical structures. In certain embodiments, this novel concept reduces hydrolytic and enzymatic degradation of both the crosslinked polymer and at the filler resin interface. In other embodiments, the step growth nature of the polymerization and the facile incorporation of inorganic fillers result in a composite with high functional group conversion, concomitantly low extractables and excellent mechanics. In yet other embodiments, that these properties reduced levels of wear and susceptibility to fatigue, thereby enabling increased service lifetimes by at least 2-fold. Finally, though methacrylates exhibit some co-polymerization tendencies toward alkynes, to develop exceptional adhesion heterofunctional moieties that incorporate both alkyne and methacrylate functional groups are characterize and developed, such that co-polymerization between the composite compositions of the invention and current commercially available adhesive systems result in an overall system with exceptional adhesion at the tooth interface.

Experimental Design:

A model azide/alkyne system with high T$_g$ and modulus has been identified, based on monomers 1 and 2 in FIG. 3. With this model system as a starting point, degradation, wear and fatigue, and adhesion are evaluated for both resin and composite systems. For the composite systems, the initial baseline evaluations utilize fillers functionalized with the trimethoxy azide silane (1) from Table 1 as this silane structurally is most similar to the commonly utilized MPS silane for the BisGMA/TEGDMA control formulations. The control system composites are filled with 70 wt % of a mixture of 0.4 µm glass (90 wt %) and OX50 (10 wt %). In certain embodiments, if the resin viscosities of the CuAAC system and the control are significantly different, rather than filling to the same weight percentage of filler, the systems are filled to the same consistency.

Integration of the Composite and Adhesive. In certain embodiments, the novel azide/alkyne system is compatible with current methacrylate-based adhesive products. Adhesion is tested using a commercially available adhesive bonding system and compared to adhesion using the control BisGMA/TEGDMA composite. This initial data provides a starting point to determine the level of additional integration that is required to generate at least equivalent adhesion to the BisGMA/TEGDMA control system. Adhesion of the formulated azide/alkyne composites in combination with available adhesive bonding systems is measured to determine a baseline adhesion level between already existing methacrylate adhesives and the novel azide/alkyne systems. Without wishing to be limited by any theory, though the interaction between the methacrylate adhesive formulation and the azide/alkyne formulation may not be ideal, some co-polymerization between methacrylate and alkyne functional groups, particularly given the nature of the photoinitiated radical formation in the photo CuAAC reaction, likely results in covalent interactions and adhesion between the two materials.

Figure 7:
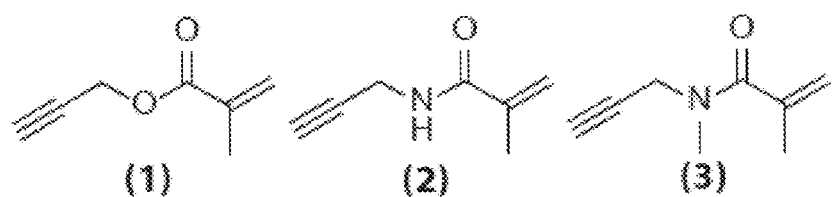
FIG. 7 illustrates monomer compatibilizers.
Figure 8:
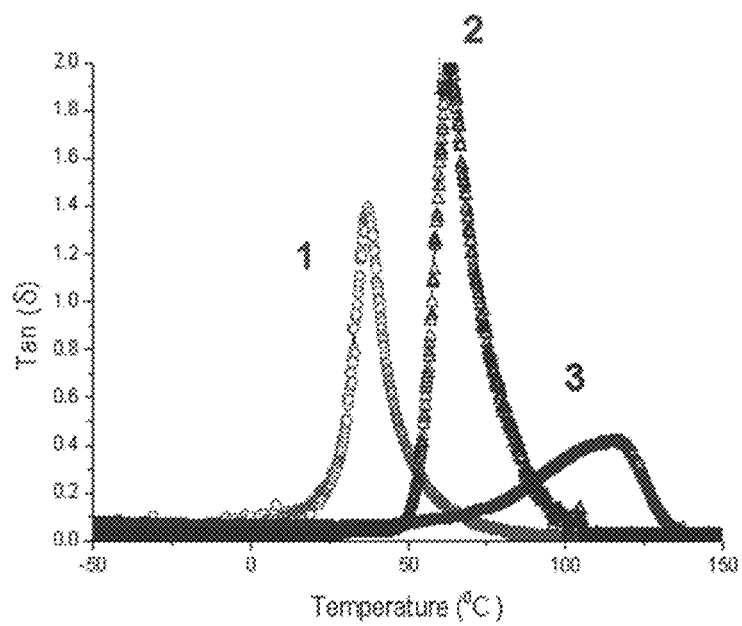
FIG. 8 illustrates glass transition temperature, $T_g$, comparison of three distinct polymers: polymer 1 was synthesized the thiol-ene monomers, polymer 2 was synthesized form photo-CuAAC reaction (aliphatic azide) monomers, and polymer 3 was synthesized from photo-CuAAC reaction (aromatic azide)
Figure 8:
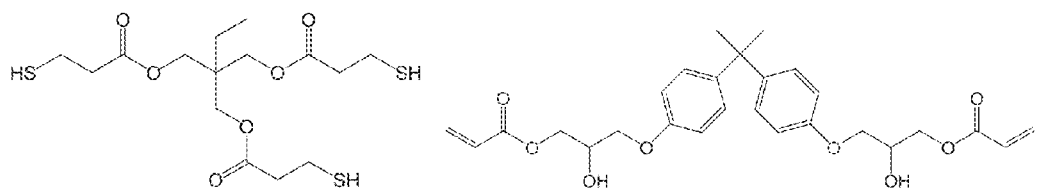
Figure 8:
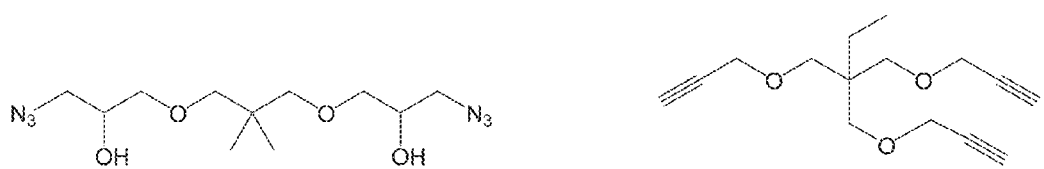
Figure 8:
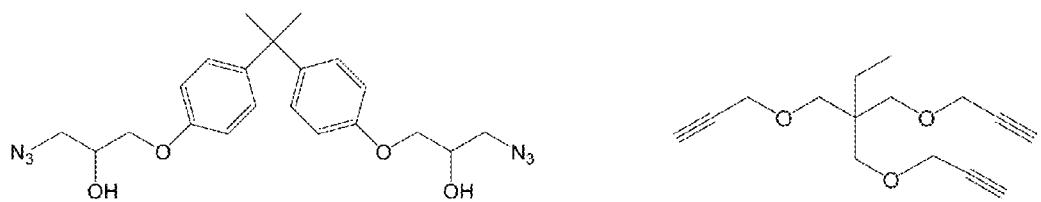
Figure 9:
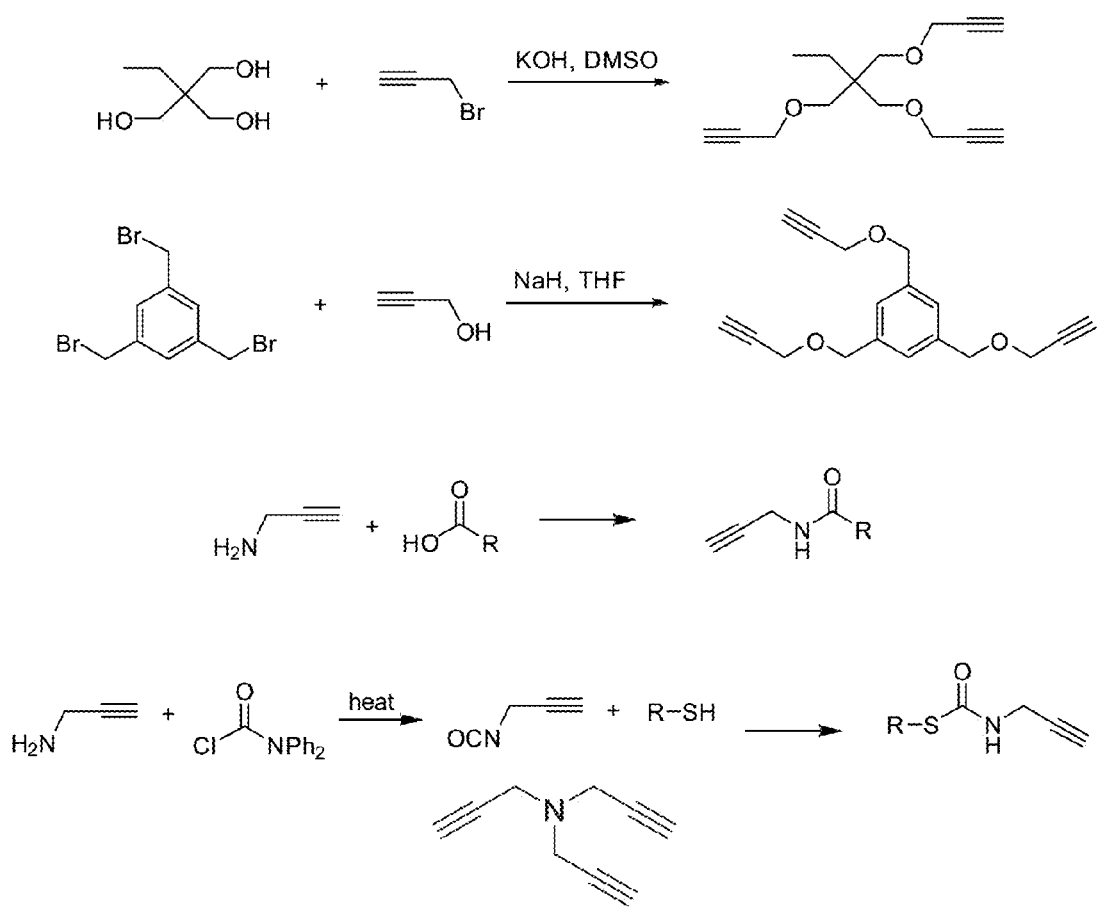
FIG. 9 illustrates the synthesis of alkyne-based substrates contemplated in the invention.
Figure 10:
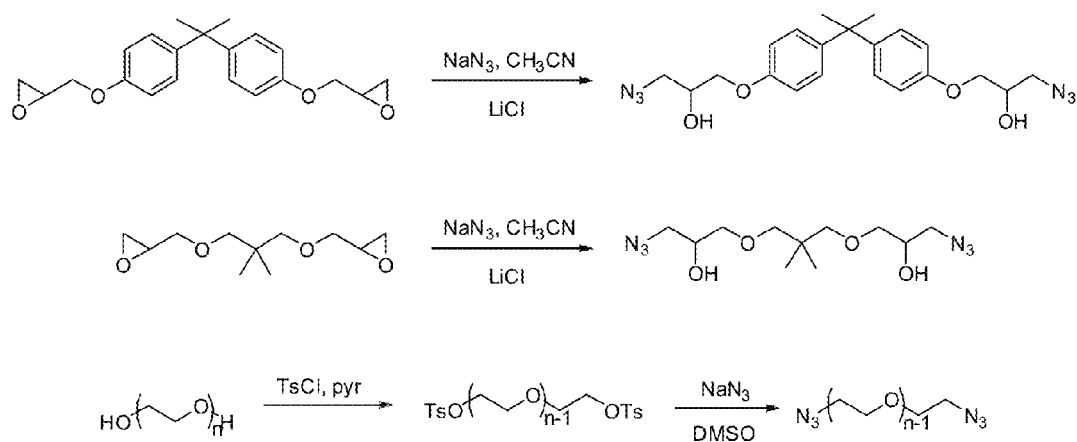
FIG. 10 illustrates the synthesis of azide-based substrates contemplated in the invention.
Figure 11:
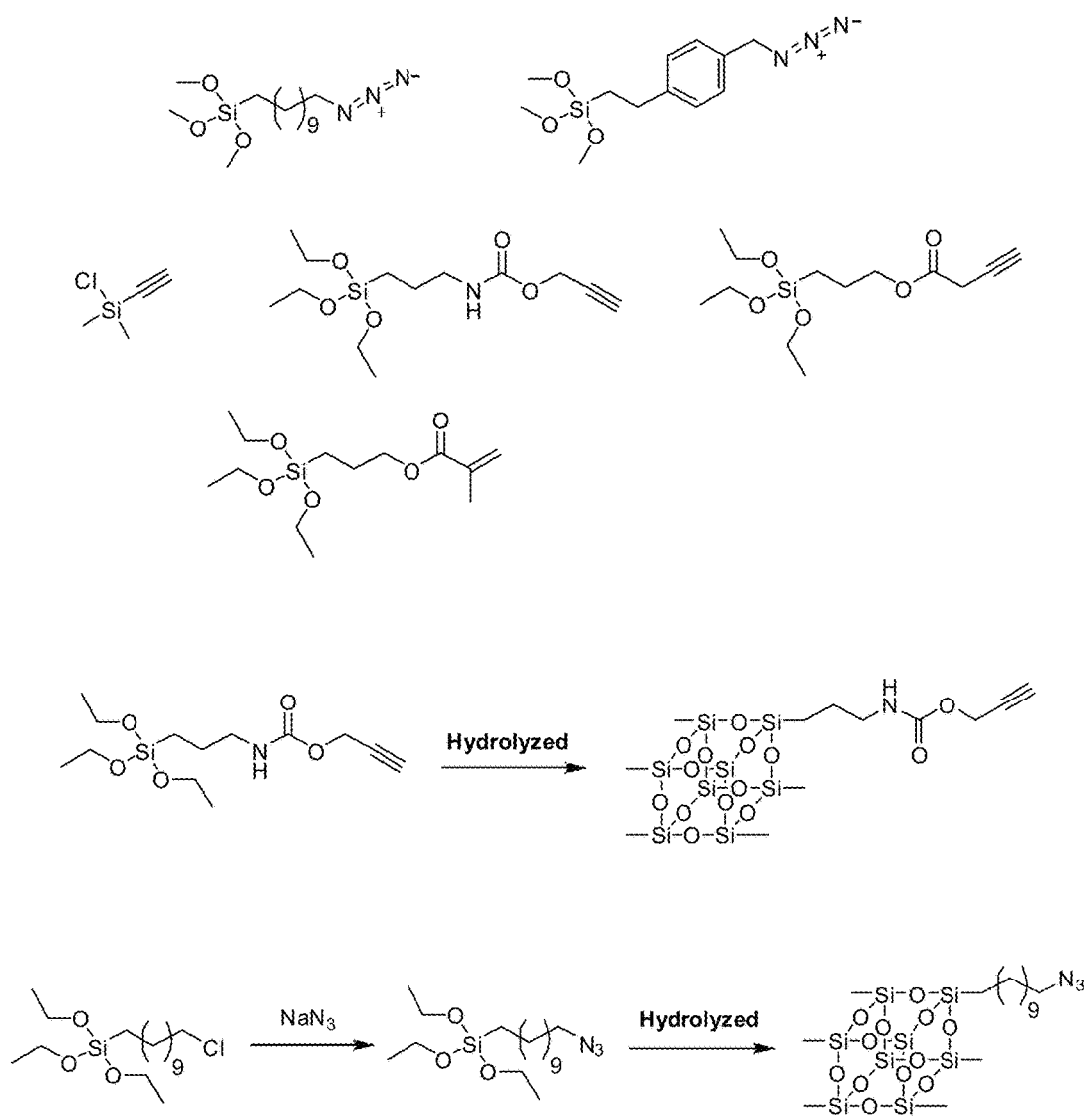
FIG. 11 illustrates silanes useful to prepare functionalized fillers contemplated in the invention.

In certain embodiments, various amounts of compatibilizers are incorporated into the composite. Adding compatibilizing components is analogous to adding "adhesion promoters" into adhesive systems, except here covalent bonds are generated between the two formulations. In other embodiments, the compatibilizer integrates two potentially orthogonal chemistries. The compatibilizer contains both alkyne and methacrylate functional groups, which copolymerize with azide—alkyne chemistry and methacrylate chemistry, respectively (FIG. 7). Structure (1) contains a hydrolysable ester linkage, and structures (2)-(3) contain an amido group. Due to the N-methylation, structure (3) may be the most resistance against hydrolysis.

Compatibilizers are separately formulated into the composite and their effect on the adhesive, mechanical and degradation properties are assessed. In certain embodiments, compatibilizers may also have a positive effect on composites with methacrylate-functionalized filler, and may used if azide and alkyne functionalized particles exhibit poor integration.

Lifetime Analysis Through Fatigue and Degradation Analysis. Composite degradation products are evaluated, identified and eliminated. In addition to the standard water sorption and solubility, the species within water are measured and analyzed via HPLC. Analysis of the soluble products is conducted on all formulations that achieve improved conversion and equivalent mechanical properties to the BisGMA/TEGDMA controls and enables the identification of degradation products that guide changes and/or further optimizations of the azide-alkyne monomers and formulations. Degradation of the composites is examined in artificial saliva, esterase solution, and pH 4 phosphate buffer solutions at 37° C. In addition to testing films, specimens with increased surface area used to accelerate degradation are formed by grinding the samples. These experiments allow to develop direct comparisons to the BisGMA/TEGDMA controls regarding the level and types of degradation products such that predictions of increased lifetime can be substantiated. Without wishing to be limited by any theory, the non-ester containing alkyne/azide systems are expected to exhibit dramatically reduced levels of hydrolytic degradation products. Degradation testing is conducted on all formulations that are significantly improved regarding reduced soluble products relative to the BisGMA/TEGDMA controls. In certain embodiments, compositions demonstrate at least a 2-fold improvement over the model BisGMA/TEGDMA system by exhibiting less than 50% of the degradation levels of the BisGMA/TEGDMA system after 90 days in solution, both in thin films and in high surface area powders.

Wear and fatigue testing are performed and correlated to other mechanics-related results obtained herein. Compositions are characterized for polymerization kinetics, final conversion, mechanics, shrinkage and stress, moisture uptake, and extractables. The initial azide/alkyne formulation (FIG. 3) is subjected to all of the testing protocols and compared to BisGMA/TEGDMA to establish baseline correlations between mechanics and extractables, wear, and degradation. Additional compositions are characterized for wear, degradation (7 days), and adhesion. In certain embodiments, compositions that achieve wear and degradation properties exhibiting at least a 2-fold improvement over the BisGMA/TEGDMA controls are characterized for fatigue. In certain embodiments, compositions achieve at least twice the number of cycles before failure at an equivalent load over the control BisGMA/TEGDMA system. In other embodiments, this combined behavior yields at least a twofold increase in service life.

Testing Protocols:

As indicated, the control BisGMA/TEGDMA system is a 70/30 wt % monomer mixture. The composite contains 70 wt % MPS functionalized filler (90% 0.4 µm glass (Schott) and 10% 40 nm OX50 (Aerosil). The initiator system is the same as for the experimental systems.

Adhesion: The "single plane shear test" is assumed herein. The test attempts to concentrate stresses uniformly across the interface of the bonding resin with the tooth and also controls for many other factors. Teeth are kept moist until the bonding procedure begins and then the proximal surfaces are flattened to dentin with silicon carbide abrasive (320 ANSI; P400 FEMA to approximate smear from cutting dentin with a bur) and mounted in the proper orientation in one Delrin block, in which the area of bonding is well defined by a 50 µm hole punched in a thick adhesive Mylar sheet covering the tooth. A second Delrin block is then screwed to the first with a larger hole aligned with the bonded interface in which the composite or resin to be tested is applied and polymerized. The exposed tooth surface is treated by etching as indicated for the bonding procedure. Bonding agents are applied and polymerized to this isolated surface with the dental bonding technique chosen. The hole in the second Delrin block is then filled with the composite restorative. The attached blocks are stored in distilled water for 24 h at 37° C. and then mounted in a mechanical testing machine with paralleling plates that align with the bonded interface. Formulations that exhibit at least equivalent adhesion to the BisGMA/TEGDMA controls are also subjected to additional media (artificial saliva, esterase, and pH 4 solutions) for 90 days at 37° C. and compared to BisGMA/TEGDMA controls. The two blocks are removed and a shear force pulled across the interface at a rate of 1 mm/min. The bond strength is recorded as the breaking force divided by the cross-sectional area of the pre-defined bonding hole. The number of specimens tested per formulation will be at least 10. Coefficient of variation from 0.2 to 0.4 have been obtained for most dentin bond strength testing. In certain embodiments, compositions exhibit at least equivalent performance to the BisGMA/TEGDMA control.

Fatigue (Long Term Performance): Cyclic deformation is of importance when evaluating fatigue and failure in dental composites. Samples are be prepared in the same manner as for flexural testing and tested in deionized water using staircase sensitivity statistical design to obtain mean and standard deviations of failure loads for 500,000 cycles (if specimen does not fail, the next specimen is tested at a higher load; if specimen fails, the load is reduced for the next test). This provides standard benchmark data. Initial screening at 2 Hz, 10 Hz and 20 Hz is done to examine potential strain-rate sensitivity. If strain-rate sensitivity is noted, then all definitive testing is done at 2 Hz, otherwise testing is performed at 20 Hz. Twenty specimens of each material are used, with 4-5 specimens tested at a step size of 50 N to approximate the 50% probability of failure load and 15-16 specimens tested at a step size of 25 N (standard deviations are sensitive to step size). Means are compared under ANOVA/Tukey with a 95% multiple range test. Data are analyzed with respect to cycles to failure within the range of clinically relevant loading limits (~30-60 MPa). Successful formulations achieve at least twice the number of cycles before failure at an equivalent load over the BisGMA/TEGDMA control.

Wear/Degradation: A 3-body wear machine (Oregon Health Sciences University Oral Wear Simulator) is used. Specimens are subjected to three-body abrasion with an abrasion load of 20 N and an attrition load of 70 N at a frequency of 1.2 Hz and 50,000 cycles. In certain embodiments, compositions exhibit less than half of the wear of the control.

Extractables: Polymer and composite samples are immersed for 7 or 90 days in deionized water, artificial saliva (aqueous solution prepared with 0.4 g/l NaCl, 0.4 g/l KCl, 0.795 g/l $CaCl_2.0.2H_2O$, 0.78 g/l $NaH_2PO_4.0.2H_2O$, 0.005 g/l $Na_2S.9H_2O$, and 1.0 g/l $CO(NH_2)_2$), and pH 4 saline/buffer. Mass loss (water sorption and solubility: ISO 4049-7.12) is measured to determine the amount of extractables. Results for both polymer and composite samples are compared to resin and composite controls. In certain embodiments, compositions exhibit less than half the extractables as the control.

Cytotoxicity (Biocompatibility): Both polymer and composite samples are tested for cytotoxicity using the ISO 10993: Biological evaluation of medical devices, Part 5: Elution Method (L-929, mouse fibroblast cells; 1×MEM extract—24 hour exposure). Samples are sent to NAMSA for cytotoxicity testing. Results for both polymer and composite samples are compared to control BisGMA/TEGDMA polymer and composite controls. In certain embodiments, compositions exhibit a toxicity grade of 0.

Degradation (Long-Term Performance): Monomer and polymer stability towards degradation are tested by subjecting individual monomers and polymerized samples (both resin and composite) for 7 or 90 day exposures at 37° C. to artificial saliva (aqueous solution prepared with 0.4 g/l NaCl, 0.4 g/l KCl, 0.795 g/l $CaCl_2.0.2 H_2O$, 0.78 g/l $NaH_2PO_4.0.2H_2O$, 0.005 g/l $Na_2S0.9H_2O$, and 1.0 g/l $CO(NH_2)_2$), enzymatic esterase solutions, and pH 4 buffered solutions. In addition to testing thin films, to maximize extraction and degradation rates, a comparison of the degradation performance of those films with solid samples that are ground with a ball mill is performed as described. The degradation and extraction products are evaluated by HPLC and/or extracted into ethyl acetate, dried, and then mixed with methanol for analysis by LCMS to detect degradation and extraction products. Results for resin and composite samples are compared to resin and composite controls. In certain embodiments, compositions exhibit less than half the amount of degradation products as the model BisGMA/TEGDMA system.

Statistical Analysis:

Error measurements for each technique are established through repetitive trials. The standard resin or composite provides the basis from which to accept or reject each hypothesis that improvement (e.g., degradation rates or extractables) or maintaining (e.g., mechanical properties) is achieved. Sample sizes are chosen to validate hypotheses to 95% confidence and vary depending on the type of experiment to be performed and its relative error.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising an alkyne-based substrate, an azide-based substrate, at least one Cu(II) salt, a Cu(I)-stabilizing tertiary amine ligand, a filler and optionally at least one photoinducible reducing agent,
   wherein the alkyne-based substrate comprises two or more reactive alkynyl groups,
   wherein the azide-based substrate comprises two or more reactive azide groups,
   wherein the filler is functionalized with at least one selected from the group consisting of an alkyne group and an azide group, and
   wherein the alkyne-based substrate, the azide-based substrate and the functionalized filler can react through a polymerization reaction to form the backbone of a polymer, wherein the functionalized filler is incorporated within the resulting composite.

2. The composition of claim 1, wherein the composition comprises at least one compound selected from the group consisting of

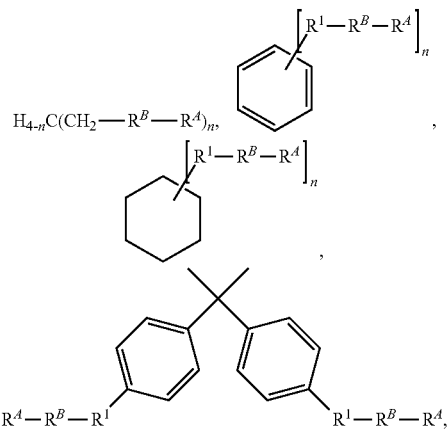

a salt or solvate thereof, and any combinations thereof, wherein:

n=2-4;

each occurrence of $R^1$ is independently a bond, —CH$_2$—, —O—, or —NR$^2$—;

each occurrence of $R^2$ is independently H or $C_1$-$C_6$ alkyl;

each occurrence of $R^B$ is independently $C_1$-$C_6$ alkanediyl, $C_1$-$C_6$ heteroalkanediyl, arenediyl, heteroarenediyl, —(CH$_2$)$_{0-4}$—NHC(=O)S—(CH$_2$)$_{0-4}$—, or —(CH$_2$)$_{0-4}$—SC(=O)NH—(CH$_2$)$_{0-4}$—;

wherein the alkanediyl, heteroalkanediyl, arenediyl and heteroarenediyl groups are optionally and independently substituted with one or more groups selected from the group consisting of OH, F, Cl, Br, I, alkyl, perfluoroalkyl, alkoxy, perfluoroalkoxy, NH$_2$, acylamino, amido, carboxyl, alkoxycarbonyl, acyloxy, formyl, acyl, thioester, carbamate, urea, sulfonate, sulfamoyl, sulfone, sulfonamide, CN, NO$_2$, and alkylthio; and each occurrence of $R^A$ is independently N$_3$ or —C≡C—H.

3. The composition of claim 1, wherein the molar ratio of the at least one reactive alkyne group and the at least one reactive azide group in the composition is such that polymerization of the composition results in greater than about 80% conversion of at least one selected from the group consisting of the alkyne-based substrate and the azide-based substrate.

4. The composition of claim 1, wherein the molar ratio of the at least one reactive alkyne group and the at least one reactive azide group in the composition ranges from about 0.5 to about 2.

5. The composition of claim 1, wherein the alkyne-based substrate and the azide-based substrate are at least partially polymerized.

6. The composition of claim 5, wherein polymerization of the substrates is achieved by irradiating at least a portion of the composition with ultraviolet, visible or infrared electromagnetic radiation.

7. The composition of claim 1, wherein the Cu(II) salt comprises at least one selected from the group consisting of copper(II) sulfate, copper(II) chloride, copper(II) bromide, copper(II) iodide, copper(II) perchlorate, copper(II) nitrate, copper(II) hydroxide, copper(II) oxide, and hydrates and mixtures thereof.

8. The composition of claim 1, wherein the composition comprises at least one photoinducible reducing agent.

9. The composition of claim 8, wherein the at least one reducing agent comprises at least one selected from the group consisting of:

1-hydroxy-cyclohexyl-phenyl-ketone(Irgacure 184);

a 1:1 mixture of 1-hydroxy-cyclohexyl-phenyl-ketone and benzophenone(Irgacure 500);

2-hydroxy-2-methyl-1-phenyl-1-propanone(Darocur™1173);

2-hydroxy-1-[4-(2-hydroxyethoxy)phenyl]-2-methyl-1-propanone(Irgacure 2959);

methyl benzoylformate(Darocur™MBF);

oxy-phenyl-acetic acid 2-[2-oxo-2-phenyl-acetoxy-ethoxy]-ethyl ester;

oxy-phenyl-acetic 2-[2-hydroxy-ethoxy]-ethyl ester;

a mixture of oxy-phenyl-acetic acid 2-[2-oxo-2-phenyl-acetoxy-ethoxy]-ethyl ester and oxy-phenyl-acetic 2-[2-hydroxy-ethoxy]-ethyl ester(Irgacure 754);

alpha,alpha-dimethoxy-alpha-phenylacetophenone(Irgacure 651);

2-benzyl-2-(dimethylamino)-1-[4-(4-morpholinyl)-phenyl]-1-butanone(Irgacure 369);

2-methyl-1-[4-(methylthio)phenyl]-2-(4-morpholinyl)-1-propanone(Irgacure 907);

a 3:7 mixture of 2-benzyl-2-(dimethylamino)-1-[4-(4-morpholinyl)phenyl]-1-butanone and alpha,alpha-dimethoxy-alpha-phenylacetophenone per weight(Irgacure 1300);

diphenyl-(2,4,6-trimethylbenzoyl) phosphine oxide (Darocur™TPO);

a 1:1 mixture of diphenyl-(2,4,6-trimethylbenzoyl)-phosphine oxide and 2-hydroxy-2-methyl-1-phenyl-1-propanone(Darocur™4265);

phenyl bis(2,4,6-trimethyl benzoyl) phosphine oxide(Irgacure 819, or Irgacure 819DW);

a 2:8 mixture of phosphine oxide, phenyl bis(2,4,6-trimethyl benzoyl) and 2-hydroxy-2-methyl-1-phenyl-1-propanone(Irgacure 2022);

phenyl-bis(2,4,6-trimethylbenzoyl)-phosphine oxide(Irgacure 2100);

bis-(eta 5-2,4-cyclopentadien-1-yl)-bis-[2,6-difluoro-3-(1H-pyrrol-1-yl)phenyl]-titanium (Irgacure 784);

(4-methylphenyl)[4-(2-methylpropyl)phenyl]-iodonium hexafluorophosphate (Irgacure 250);

2-(4-methylbenzyl)-2-(dimethylamino)-1-(4-morpholinophenyl)-butan-1-one(Irgacure 379);

4-(2-hydroxyethoxy)phenyl-(2-hydroxy-2-propyl)ketone (Irgacure 2959);

bis-(2,6-dimethoxybenzoyl)-2,4,4-trimethylpentylphosphine oxide;

a mixture of bis-(2,6-dimethoxybenzoyl)-2,4,4-trimethylpentylphosphine oxide and 2-hydroxy-2-methyl-1-phenyl-propanone(Irgacure 1700);

acyl germane photoinitiators;

titanium dioxide;

camphorquinone/amine systems;

primary amines;

and mixtures thereof.

10. The composition of claim 1, wherein the Cu(I)-stabilizing ligand comprises at least one selected from the group consisting of TBTA (tris[(1-benzyl-1H-1,2,3-triazol-4-yl)methyl]amine);

BTTES (2,4-(bis-1-tert-butyl-1H-1,2,3-triazol-4yl)methylamino(methyl-1H-1,2,3-triazol-1-yl)ethanesulfonic acid);

PMDETA (N$^1$-(2-(dimethylamino)ethyl)-N$^1$,N$^2$,N$^2$-trimethylethane-1,2-diamine);

N$^1$,N$^1$'-(ethane-1,2-diyl)bis(N$^1$,N$^2$,N$^2$-trimethylethane-1,2-diamine);

2,2'-bipyridine, and any combinations thereof.

11. The composition of claim 1, wherein the composition further comprises at least one selected from the group consisting of a bonding agent, a coupling agent, and any combinations thereof.

12. The composition of claim 1, wherein the composition further comprises a dimethacrylate monomer.

13. The composition of claim 12, wherein the dimethacrylate monomer comprises bisphenol A dimethacrylate (BisGMA) or triethyleneglycol dimethacrylate (TEGMA).

14. The composition of claim 12, wherein the composition further comprises a compatibilizer comprising an alkynyl group and an alkenyl group.

15. The composition of claim 14, wherein the compatibilizer is selected from the group consisting of prop-2-yn-1-yl methacrylate, prop-2-yn-1-yl acrylate, N-(prop-2-yn-1-yl)methacrylamide, N-(prop-2-yn-1-yl) acrylamide, N-methyl-N-(prop-2-yn-1-yl)methacrylamide, N-methyl-N-(prop-2-yn-1-yl)acrylamide, and any combinations thereof.

16. A method of preparing a dental composite composition, comprising photopolymerizing at least a portion of the at least partially unpolymerized composition of claim 1, thereby generating the dental composite composition.

17. The method of claim 16, wherein photopolymerization comprises irradiating at least a portion of the composition with ultraviolet, visible or infrared electromagnetic radiation.

18. The method of claim 16, wherein the dental composite composition has about twice or higher the service lifetime, or about equivalent or better adhesion performance, or about twice or higher the fatigue performance, or about half or lower the wear/tear performance, and/or about half or less the degradation performance, of a BisGMA/TEGDMA composite.

19. The composition of claim 1, wherein the filler comprises a $TiO_2$ nanoparticle.

20. The composition of claim 19, wherein the $TiO_2$ nanoparticle is the only photoinducible reducing agent in the composition.

* * * * *